United States Patent [19]

Kinast et al.

[11] Patent Number: 4,871,747

[45] Date of Patent: Oct. 3, 1989

[54] 3-AMINO-4,5-DIHYDROXYPIPERIDINES, PROCESS FOR THEIR PREPARATION AND THEIR USE

[75] Inventors: Günther Kinast; Matthias Schüller; Theo Schröder, all of Wuppertal, Fed. Rep. of Germany

[73] Assignee: Bayer Aktiengesellschaft, Leverkusen, Fed. Rep. of Germany

[21] Appl. No.: 937,645

[22] Filed: Dec. 3, 1986

[30] Foreign Application Priority Data

Dec. 20, 1985 [DE] Fed. Rep. of Germany ....... 3545463
Jun. 20, 1986 [DE] Fed. Rep. of Germany ....... 3620645

[51] Int. Cl.$^4$ ................... A61K 31/445; C07D 211/42
[52] U.S. Cl. ..................................... 514/315; 514/328; 546/219; 546/220; 546/242
[58] Field of Search ................ 514/315, 328; 546/219, 546/220, 242

[56] References Cited

U.S. PATENT DOCUMENTS

| | | | |
|---|---|---|---|
| 4,182,767 | 1/1980 | Murai et al. ..................... | 546/242 X |
| 4,220,782 | 9/1980 | Stoltefuss ........................... | 546/242 |
| 4,278,683 | 7/1981 | Stoltefuss et al. .................. | 546/219 |
| 4,328,233 | 5/1982 | Boshagen et al. ............... | 546/242 X |
| 4,611,058 | 9/1986 | Koebernick ......................... | 546/242 |

FOREIGN PATENT DOCUMENTS 0000947  3/1979  European Pat. Off. .

OTHER PUBLICATIONS

Chemistry Letters, Nr. 7, (1986), pp. 1051–1054; G. W. J. Fleet et al.: "Synthesis of 2-Acetamido-1,5-1,2,5-Tride Oxy-D-Mannitol and of 2-Acetamido-1,5-Imino-1,2,5-Tride Oxy-D-Glucitol, a Potent and Specific Inhibitor of a Number of Beta-N-Acetyl-glucosaminidases".

*Primary Examiner*—Joseph Paul Brust

*Attorney, Agent, or Firm*—Sprung Horn Kramer & Woods

[57] ABSTRACT

A 3-amino-4,5-dihydroxy-piperidine compound of the formula (I)

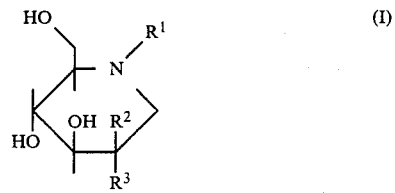

in which
 R$^1$ represents hydrogen, alkyl having up to 8 carbon atoms, aralkyl having 7 to 14 carbon atoms, or represents a group of the formula

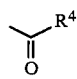

R$^4$ denotes straight-chain or branched alkyl having up to 8 carbon atoms, straight-chain or branched alkoxy having up to 8 carbon atoms, or aralkoxy having up to 10 carbon atoms, and
R$^2$ and R$^3$ represent hydrogen or represent the group NHR$^5$,
R$^5$ having the same meaning as R$^1$ and being identical to or different from the latter, with the proviso that, in every case, one substituent of R$^2$ or R$^3$ represents hydrogen and the other substituent of R$^2$ or R$^3$ represents NHR$^5$, and physiologically acceptable salts thereof. Such compound is useful to treat prediabetes, gastritis, constipation, caries, atherosclerosis, obesity, diabetes and hyperlipoproteinaemia.

19 Claims, 21 Drawing Sheets

3-AMINO-4,5-DIHYDROXYPIPERIDINES, PROCESS FOR THEIR PREPARATION AND THEIR USE

BACKGROUND OF THE INVENTION

1. Field of the Invention

The invention relates to 3-amino-4,5-dihydroxypiperidines, to a process for their preparation and to their use in medicaments, in particular for influencing lipid and carbohydrate metabolism.

2. Background Information

It is known that 1-deoxynojirimycin has an inhibitory action on glucosidases [compare E. Truscheit, W. Frommer, B. Junge, L. Müller, D. Schmidt, W. Wingender, Angew. Chem., 93, 738 (1981)].

SUMMARY OF THE INVENTION

The present invention relates to 3-amino-4,5-dihydroxypiperidines of the general formula (I)

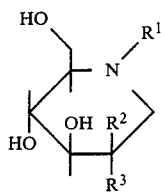

in which $R^1$ represents hydrogen, alkyl having up to 8 carbon atoms, aralkyl having 7 to 14 carbon atoms, or represents a group of the formula

$R^4$ denoting straight-chain or branched alkyl having up to 8 carbon atoms, straight-chain or branched alkoxy having up to 8 carbon atoms, or aralkoxy having up to 10 carbon atoms, and $R^2$ and $R^3$ represent hydrogen or represent the group $NHR^5$, $R^5$ having the same meaning as $R^1$ and being identical to or different from the latter, with the proviso that, in every case, one substitutent of $R^2$ or $R^3$ represents hydrogen and the other substituent of $R^2$ or $R^3$ represents $NHR^5$, and physiologically acceptable salts thereof.

Preferred compounds of the general formula (I) are those in which $R^1$ represents hydrogen or alkyl having up to 6 carbon atoms, $R^1$ represents benzyl or $R^1$ represents a group of the formula

in which $R^4$ denotes straight-chain or branched alkyl having up to 4 carbon atoms, straight-chain or branched alkoxy having up to 4 carbon atoms, or benzyloxy, and $R^2$ and $R^3$ represent hydrogen or represent $NHR^5$, $R^5$ having the same meaning as $R^1$ and being identical to or different from the latter, with the proviso that, in every case, one substituent $R^2$ or $R^3$ represents hydrogen and the other substituent $R^2$ or $R^3$ represents $NHR^5$, and physiologically acceptable salts thereof.

Particularly preferred compounds of the general formula (I) are those in which $R^1$ represents hydrogen, alkyl having up to 4 carbon atoms, benzyl, acetyl or benzyloxycarbonyl, and $R^2$ and $R^3$ represent hydrogen or represent the group $NHR^5$, $R^5$ having the same meaning as $R^1$ and being identical to or different from the latter, with the proviso that, in every case, one substituent $R^2$ or $R^3$ represents hydrogen and the other substituent $R^2$ or $R^3$ represents $NHR^5$, and physiologically acceptable salts thereof.

Physiologically acceptable salts are, in general, salts of the compounds according to the invention with inorganic or organic acids. These preferably include hydrochlorides, hydrobromides, sulphates, hydrogen sulphates, hydrogen phosphates, hydrogen carbonates, carbonates, phosphates, acetates, maleates, citrates, fumarates, oxalates or benzoates.

The general formula (I) within the scope of the present invention comprises both the derivatives having the D-manno configuration (Ia) and the derivatives having the D-gluco configuration (Ib). The derivatives having the manno configuration (Ia) represent, according to the invention, compounds of the following formula:

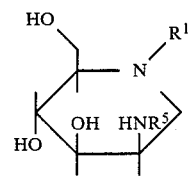

The derivatives having the gluco configuration (Ib) represent, according to the invention, compounds of the following formula:

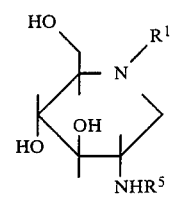

The derivatives having the manno configuration, of the general formula (Ia)

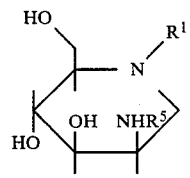

in which $R^1$ represents hydrogen, alkyl having up to 8 carbon atoms, aralkyl having 7 to 14 carbon atoms, or represents a group of the formula $R^4$ denoting straight-chain or branched alkyl having up to 8 carbon atoms, straight-chain or branched alkoxy having up to 8 carbon atoms, or aralkoxy having up to 10 carbon atoms, and $R^5$ has the same meaning as $R^1$ and is identical to or different from the latter, and physiologically acceptable salts thereof, are obtained by cyclization, under reductive conditions, in inert solvents, of the compound of the formula (II)

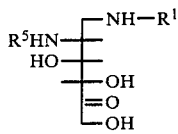

in which $R^1$ represents an amino protective group, preferably benzyloxycarbonyl, benzyl or tert.-butyloxycarbonyl, and does not denote hydrogen, and $R^5$ represents an amino protective group different from $R^1$, preferably an acetyl, where appropriate elimination of protective groups, where appropriate introduction of new protective groups, and where appropriate then preparation with acids of the corresponding salts.

The process can be illustrated by, for example, the following diagram:

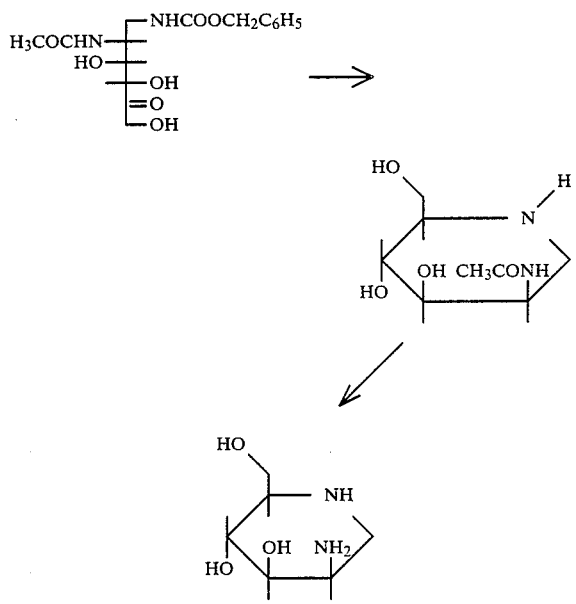

The reductive cyclization is generally carried out in the presence of a reducing agent, where appropriate in the presence of a catalyst.

The cyclization is preferably carried out using hydrogen as the reducing agent. Catalysts which are suitable for this are noble metal catalysts such as Pd and Pt, preferably Pd on animal charcoal.

Solvents which are suitable for this are water and all inert organic solvents which do not change under the reaction conditions. These preferably include alcohols such as methanol, ethanol, propanol or isopropanol, ethers such as diethyl ether, dioxane, tetrahydrofuran or glycol dimethyl ether, dimethylformamide or glacial acetic acid. It is equally possible to use mixtures of the said solvents.

In general, the reaction is carried out under a pressure of hydrogen of 1 to 150 bar, preferably of 1 to 100 bar.

In general, the reaction is carried out in a temperature range from 20° to 150° C., preferably from 20° to 100° C.

Furthermore, suitable reducing agents are alkali metal cyanoborohydrides, dialkylaminoboranes or alkali metal borohydrides.

The solvents which can be used are the same solvents as in the cyclization with hydrogen. Particularly suitable for this are mixtures of water with alcohols or dimethylformamide.

The reductive cyclization is generally carried out under atmospheric pressure and at a temperature range from 0° C. to 150° C., preferably from 20° C. to 100° C.

The process according to the invention is generally carried out in a pH range from 1 to 11, preferably from 4 to 9, depending on the nature of the protective groups $R^1$ which are present and which are eliminated in situ in the reductive cyclization without, at the same time, $R^5$ being eliminated.

The elimination of protective groups and the introduction of new protective groups is generally carried out by customary methods as are described in, for example, Houben-Weyl's "Methoden der organischen Chemie" (Methods of Organic Chemistry) XV/1 and 2 and with which the expert is familiar.

DETAILED DESCRIPTION OF THE INVENTION

The compounds of the general formula (II) which are used as starting materials are new. They can be prepared by methods known per se, for example in accordance with the following scheme:

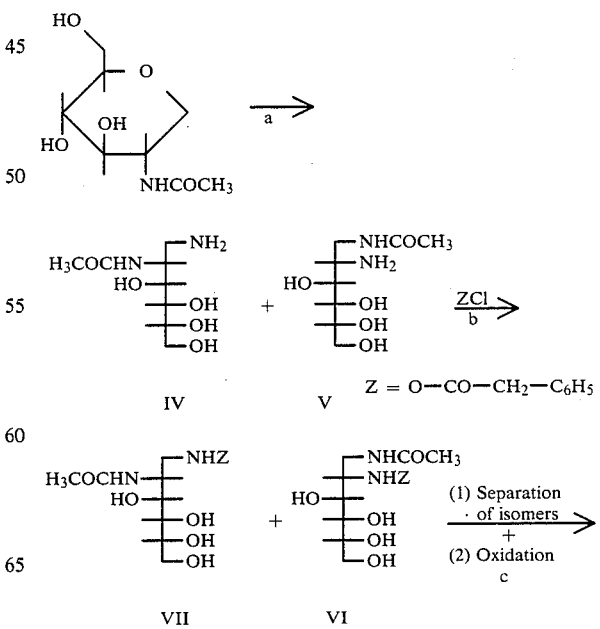

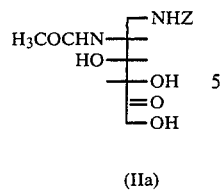

(IIa)

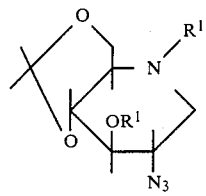

(VIII)

This entails, in step a, hydrogenation of N-acetyl-glucosamine III in inert solvents such as, for example, water, alcohols, for example methanol, ethanol, propanol or isopropanol or mixtures of the said solvents, in the presence of catalysts such as Raney nickel, in the presence of ammonia, at temperatures from 20° to 200° C., preferably from 1° to 150° C., under a pressure of 1 to 200 bar, preferably of 1 to 150 bar, this resulting in the mixture of the open-chain isomeric compounds IV and V. In step b, this mixture is, without previous separation, reacted with benzyloxycarbonyl chloride in inert solvents such as water or alcohols, for example methanol, ethanol, propanol or isopropanol or their mixtures, in the presence of a base such as sodium or potassium carbonate, at temperatures from −20° C. to +80° C., preferably from 0° C. to +40° C., and the mixture of products VI and VII is separated by customary chromatographic processes. In the last step c, finally the isomer having the manno configuration is oxidized by methods known per se to give the compound II, preferably by a microbiological process using Glucobacter cells as described, for example, by G. Kinast, M. Schedel in *Angew. Chem. Int. Ed.*, 20 (9) 805 (1981).

The derivatives having the gluco configuration, of the general formula (Ib)

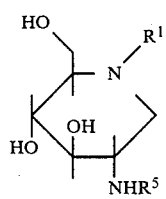

(Ib)

in which $R^1$ represents hydrogen, alkyl having up to 8 carbon atoms, aralkyl having 7 to 14 carbon atoms, or represents a group of the formula

$R^4$ denoting straight-chain or branched alkyl having up to 8 carbon atoms, straight-chain or branched alkoxy having up to 8 carbon atoms, or aralkoxy having up to 10 carbon atoms, and $R^5$ has the same meaning as $R^1$ and is identical to or different from the latter, and physiologically acceptable salts thereof, are obtained by reduction, in inert solvents in the presence of a reducing agent, where appropriate in the presence of a catalyst, of azido compounds of the formula (VIII)

in which $R_1$ represents an aminoprotective group, preferably benzyl, where appropriate elimination of protective groups, where appropriate introduction of new protective groups $R^5$, and where appropriate then preparation with acid of the corresponding salts.

The reduction is generally carried out by the methods which are customary for the reduction of azides to amino groups.

These include reduction with hydrogen as reducing agent in the presence of a catalyst such as Raney nickel, Pd or Pt (where appropriate on animal charcoal), where appropriate in the presence of acids such as sulphonic acids (for example methane-, benzene- or toluenesulphonic acid) or mineral acids (for example HCl, $H_2SO_4$ or HBr) or carboxylic acids (acetic acid or trifluoroacetic acid) in inert solvents such as water, alcohols, for example methanol, ethanol, propanol or isopropanol, dimethylformamide or mixtures thereof, or reduction with hydrides as reducing agents such as, for example, sodium borohydride, lithium alanate or sodium cyanoborohydride, where appropriate with nickel salts in inert solvents such as water, alcohols such as methanol, ethanol, propanol or isopropanol, or dimethylformamide, or mixtures of the said solvents, and reduction with hydrogen sulphide in pyridine.

Other reducing processes for azides which can be employed according to the invention are described in Houben-Weyl's "Methoden der organischen Chemie" X/3, 822, XI/1, 539.

The elimination of protective groups and the reintroduction of new protective groups is generally carried out by customary methods as are described in, for example, Houben-Weyl's "Methoden der organischen Chemie" XV/1 and 2 and Baker and Ollis' "Comprehensive Organic Chemistry", 5, 714. They are known and are familiar to the expert.

The azido compounds of the formula VIII which are used as starting materials are new. However, they can be prepared by methods which are known in principle, in accordance with the following scheme:

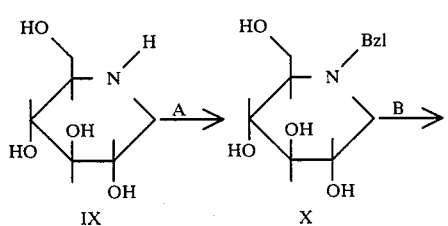

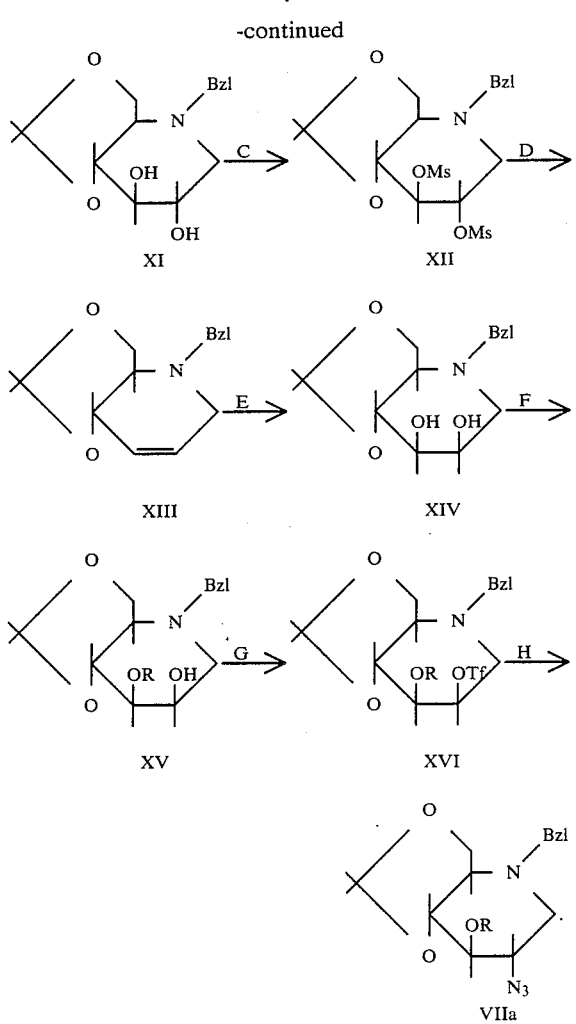

Bzl. = CH₂C₆H₅
Ms = mesyl
Tf = trifluoromethylsulphonyl
R = Bzl. or p-methoxy-benzyl According to this, in step A, deoxynojirimycin (disclosed in EP-OS (European Published Specification) No. 947) is benzylated with benzyl bromide and potassium carbonate in dimethylformamide and cooled in ice to give X. In step B, the benzyl compound X is, after removal of the potassium carbonate, reacted with acids (pH 2) and 2-methoxypropene or 2,2-dimethoxypropane in dimethylformamide to give XI and, in step C, XI is converted with methanesulphonyl chloride in acetone/triethylamine into the mesylate XII. By reaction of XII with NaI/Zn in dimethylformamide (step D) there is obtained the olefin XIII which is then hydroxylated (step E) with OsO₄/N-methylmorpholine N-oxide to give XIV. In step F, the derivative XIV, which has the manno configuration, is, via a bis-dibutyltin acetal, which is generated in situ, stereoselectively benzylated with benzyl bromide or p-methoxybenzyl chloride and tetrabutylammonium bromide to give XV. In step G, XV is converted with trifluoromethanesulphonic anhydride in CH₂Cl₂/pyridine at −20° C. into XVI, and then XVI is converted (step H) with LiN₃ in a CH₂Cl₂/dimethylformamide mixture at −40° C. stereoselectively into the azide VIIa, with inversion at C-2.

The compounds according to the invention have interesting pharmacological actions. They inhibit extra- and intracellular carbohydrate metabolism, glycosyl transferases and glucosidases. Furthermore, they have effects on glycoprotein and chitin biosynthesis and have fungicidal, bacteriostatic and immunomodulatory actions.

By reason of their properties, they can be used, for example, as therapeutic agents for the following diseases: prediabetes, gastritis, constipation, caries, atherosclerosis, obesity, diabetes or hyperlipoproteinaemia.

The compounds can be administered without dilution, for example as powders or in a gelatin case, or in combination with a vehicle in a pharmaceutical composition. Pharmaceutical compositions can contain a larger or smaller amount of the active compound, for example 0.1% to 99.5%, in combination with a pharmaceutically tolerated non-toxic, inert vehicle, it being possible for the vehicle to contain one or more solid, semisolid or liquid diluents, fillers and/or non-toxic, inert and pharmaceutically tolerated formulating auxiliaries. Pharmaceutical preparations of this type are preferably in the form of dosage units, that is to say physically discrete units which contain a defined amount of the active compound and correspond to a fraction or a multiple of the dose required for bringing about the desired effect. The dose units can contain 1, 2, 3, 4 or more single doses or ½, ⅓ or ¼ of a single dose. A single dose preferably contains an amount of active compound which suffices to achieve the desired effect on administration in accordance with a predetermined dosage regimen of one or more dosage units, there being administration of a whole, a half, a third or a quarter of the daily dose, usually at the times of all main meals and snacks during the day.

It is also possible for other therapeutic agents to be taken. Although careful consideration ought to be given to the dosage and the dosage regimen in each case, by application of well-founded expert judgment and taking into account the age, the weight and the condition of the patient and the nature and severity of the disease, the dosage will usually be in a range between about 1 to about 1×10⁴ SIU/kg of body weight per day. In some cases, an adequate therapeutic effect will be achieved with a lower dose than this, whereas in other cases a larger dose will be necessary.

Oral administration can be carried out by use of solid and liquid dosage units, for example as powders, tablets, coated tablets, capsules, granules, suspensions, solutions and the like.

Powder is prepared by comminuting the substance to a suitable size, and mixing with a, likewise comminuted, pharmaceutical vehicle. Although an edible carbohydrate, such as, for example, starch, lactose, sucrose or glucose, is normally used for this purpose and can also be utilized in this instance, it is desirable to utilize a carbohydrate which is not metabolized such as, for example, a cellulose derivative.

Sweeteners, flavoring additives, preservatives, dispersing agents and colorants can also be used too.

The capsules can be prepared by preparation of the powder mixtures described above and by introduction into gelatin cases which have already been formed. The powder mixtures can be mixed, before the introduction process, with lubricants such as, for example, silica gel, talc, magnesium stearate, calcium stearate or solid polyethylene glycol.

The mixture can likewise be mixed with a disintegrant or solubilizer such as, for example, agar-agar, calcium carbonate or sodium carbonate in order to improve the availability of the active compound when the capsule is taken.

The tablets are prepared by, for example, preparation of a powder mixture, coarse or fine-grain, and addition of a lubricant and disintegrant. Tablets are shaped from this mixture. A powder mixture is prepared by mixing the substance, which has been comminuted in a suitable manner, and supplementation by a diluent or another vehicle as described above. Where appropriate, a binder is added, for example carboxymethylcellulose, alginates, gelatin or polyvinylpyrrolidones, a solution retardant such as, for example, paraffin, an absorption accelerator such as, for example, a quaternary salt and/or an adsorbent such as, for example, bentonite, kaolin or dicalcium phosphate. The powder mixture can be granulated together with a binder such as, for example, syrup, starch paste, acacia mucilage or solutions of cellulosic or polymeric material. The product is then forced through a coarse screen. As an alternative to this, the powder mixture can be allowed to run through a tabletting machine, and the resulting irregularly shaped pieces can be comminuted to the size of grains. In order to stop the resulting grains from sticking in the nozzles, they can be mixed with a lubricant such as, for example, stearic acid, stearate salt, talc or mineral oil. This lubricated mixture is then pressed in the form of tablets. The active compounds can also be mixed with free-flowing, inert vehicles and directly converted into the form of tablets, omitting the granulation and comminution steps. The product can be provided with a clear or opaque protective coating, for example a covering of shellac, a covering of sugar or polymeric substances and a polished wax coating. Colorants can be added to these coverings so that it is possible to distinguish between the individual dosage units.

The presentations which are administered orally, for example solutions, syrups and elixirs, can be prepared in dosage units so that a particular amount of product contains a particular amount of active compound. Syrup can be prepared such that the active compound is dissolved in an aqueous solution which contains suitable flavourings. Elixirs are obtained by use of non-toxic, alcoholic vehicles. Suspensions can be prepared by dispersion of the compound in a non-toxic vehicle. Solubilizers and emulsifiers, such as, for example, ethoxylated isostearyl alcohols and polyoxyethylene sorbitol esters, preservatives, flavor-improving additives such as, for example, peppermint oil or saccharin and the like can also be added.

Dosage instructions can be indicated on the capsule. Furthermore, the dosage can be safeguarded in such a way that the active compound is released in a delayed manner, for example by restraining the active compound in polymeric substances, waxes and the like.

In addition to the abovementioned pharmaceutical compositions, it is also possible to prepare foodstuffs containing the latter, for example sugars, bread, potato products, fruit juice, beer, chocolate or other items of confectionery, and conserves such as, for example, jam, there being added to these products an effective amount of at least one of the active compounds according to the invention. The foodstuffs prepared using the active compounds according to the invention are suitable both for the diet of patients who are suffering from metabolic disorders and for the nutrition of healthy people in the sense of a mode of nutrition preventing a metabolic disorder.

Furthermore, the compounds according to the invention exhibit the properties of having a great effect on the ratio of the fraction of undesired fat to the fraction of desired low-fat meat in animals in favor of lean meat. This is of particular importance for the rearing and maintenance of other useful and ornamental animals. Furthermore, the use of the active compounds can result in considerable economy in the feeding of the animals, both in terms of time, in terms of amounts and in terms of quality. Since they bring about a certain delay in digestion, the residence time of the nutrients in the digestive tract is prolonged, which makes possible ad libitum feeding which is associated with less effort. Furthermore, when the substances according to the invention are used there is in many cases a considerable saving in valuable protein feed.

The active compounds can thus be used in virtually all areas of animal nutrition as agents for reducing obesity and saving feed protein.

The efficacy of the active compounds for this is substantially independent of the species and the sex of the animals. The active compounds prove to be especially valuable in animal species which are prone, intrinsically or in certain periods of life, to relatively heavy fatty deposits.

PREPARATION EXAMPLES

Example 1

2-Acetamido-1-amino-1,2-dideoxy-D-mannitol

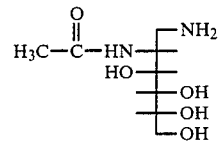

221 g (1 mol) of acetylglucosamine were dissolved in 2 l of methanol, and 20 g of Raney nickel and 250 ml of concentrated $NH_3$ were added, and the mixture was hydrogenated with 100 bar of $H_2$ at 100° C. for 5 hours. For the working up, the catalyst is removed by filtration with suction, and the batch is evaporated to dryness. The resulting crude product is reacted, without further purification, as indicated in Example 2.

Example 2

2-Acetamido-1-benzyloxycarbonylamino-1,2-dideoxy-D-mannitol

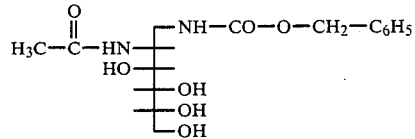

The crude product from Example 1, which is free of $NH_3$ owing to thorough drying in vacuo over concentrated $H_2SO_4$, is dissolved in 250 ml of water and, while cooling in ice and stirring, 150 g (1.1 mol) of benzyloxycarbonyl chloride and 150 g (1.1 mol) of $K_2CO_3$ are added, and the mixture is stirred at room temperature for 18 hours. The precipitate is then removed by filtration with suction, the filtrate is evaporated to dryness, and the residue is fractionated on RP8 (laboratory column supplied by Merck, size C). For this purpose, 2 columns are connected in series, 20 g of the residue is dissolved in about 200 ml of H₂O, the resulting solution is applied to the column, and then elution is carried out at a flow rate of about 15 ml/min with 1.5 l of H₂O/CH₃CN 90/10 and 1.5 l of H₂O/CH₃CN 80/20. The fractions are examined by HPLC (column: Li Chrosorb/RP8 (10 μm), 2 ml/min buffer pH 7/CH₃CN 80/20, 210 nm) and the fractions with a retention time of 3.35 minutes are combined, the acetonitrile is removed by evaporation in vacuo, and the residue is freeze-dried. 1 to 2 g of the pure product are obtained from 20 g of the residue applied.

Example 3

5-Acetamido-6-benzyloxycarbonylamino-5,6-dideoxy-D-fructose

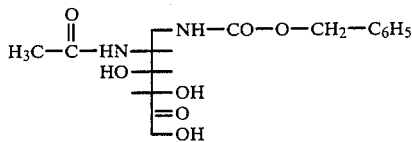

4 g of Glucobacter cells are suspended in 100 ml of 0.1M phosphate buffer pH 4.5 (made up with tap water) and 1.2 g of acetamido-1-benzyloxycarbonylamino-1,2-dideoxy-D-mannitol are added. The mixture is left to shake at 32° C. overnight. After 30 hours, it is centrifuged, and the residue is washed twice with 100 ml of methanol. The supernatant and the methanol extracts are combined and evaporated to dryness. The crude product is processed further without working up.

Example 4

2-Acetamido-1,5-imino-1,2,5-trideoxy-D-mannitol

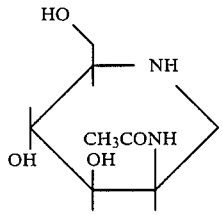

0.6 g of the product from Example 3, 1.1 g of Pd/C (5%) and 3 mg of K₂CO₃ are dissolved in 25 ml of H₂O and 50 ml of methanol, and hydrogenation is carried out with 50 atm at 60° C. for 4 hours. For the working up, the catalyst is removed by filtration, and the filtrate is passed through a column containing an acid ion exchanger (Lewatit SP 112, H form) which is washed with H₃COH/H₂O 80/20, and then the crude product is eluted with H₃COH/concentrated NH₃, and the fractions containing the product (TLC system: CHCl₃/CH₃OH/concentrated NH₃ 4:3:1) are evaporated in a rotary evaporator and recrystallized from H₂O/H₃COH. Yield: 0.21 g FIG. 1 shows the ¹H NMR spectrum of the compound of Example 4 (250 MHz/D₂O)

Example 5

2-Amino-1,5-imino-1,2,5-trideoxy-D-mannitol

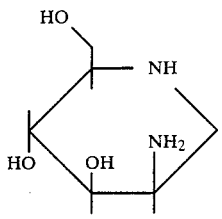

The compound from Example 4 (0.5 g) was heated to reflux in 2N NaOH for 2 hours, and the product was neutralized with 2N HCl and purified on an acid ion exchanger as indicated in Example 3.

Yield: 0.2 g

Example 6

N-Benzyl-1,5-dideoxy-1,5-imino-D-glucitol

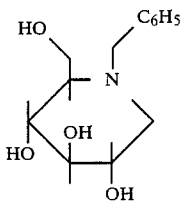

163.2 g (1.0 mol) of deoxynojirimycin are dissolved in 2.5 l of dimethylformamide. 76.0 g (0.55 mol) of potassium carbonate are added to the solution. After cooling to 0° C., 188.1 g (1.1 mol) of benzyl bromide are added dropwise over the course of 30 minutes. After about 120 minutes the starting material has completely reacted. The product is processed further in situ.

A small portion is removed for characterization, purified, after removal of the solvent, by column chromatography on silica gel in the system chloroform/methanol=4:1, and obtained as crystalline solid. Melting point: 181° C. $[\alpha]_D^{20} = -48.3°$ (methanol)

Example 7

N-Benzyl-4,6-O-isopropylidene-1,5-dideoxy-1,5-imino-D-glucitol

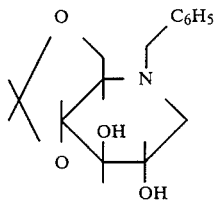

After the sediment has been removed from the reaction mixture from Example 6 by filtration, sufficient p-toluenesulphonic acid is added to adjust the pH to 1.5. Then a mixture of 208 g (2 mol) of dimethoxypropane and 144 g (2 mol) of 2-methoxy-propene is added. After a reaction time of 2 hours at 30° C., thin-layer chromatography in toluene:ethanol=3:1 establishes that the reaction is complete. The working up is carried out by stirring for several hours with a suspension of 210 g of sodium bicarbonate in 100 ml of water. After the solvent has been removed by evaporation, the residue is digested with chloroform, and the chloroform phase is washed, dried over sodium sulphate and, after removal of the solvent by evaporation, the residue is recrystallized from ethyl acetate/petroleum ether.

Yield: 249.3 g

Melting point: 117° C. $[\alpha]_D^{20} = -100.3°$ (methanol)

Example 8

N-Benzyl-4,6-O-isopropylidene-2,3-di-O-mesyl-1,5-dideoxy-1,5-imino-D-glucitol

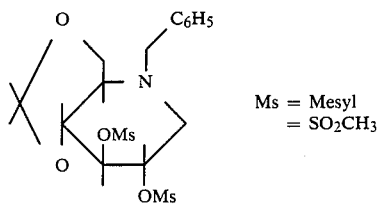

Ms = Mesyl = SO₂CH₃

240 g (0.81 mol) of the product from Example 7 are dissolved in 2,000 ml of acetone and 300 ml of triethylamine (2.1 mol). To this is slowly added dropwise, while cooling in ice, a solution of 138 ml (1.8 mol) of methanesulphonyl chloride in 600 ml of acetone. Then the ice-bath is removed, and the mixture is stirred at room temperature overnight. After reaction is complete (TLC toluene/acetone 4:1), first the precipitated salts are removed by filtration and then excess mesyl chloride is hydrolyzed with a little ice, and the mixture is evaporated in a rotary evaporator. The crystalline residue is taken up in methylene chloride, and the organic phase is washed with water, dried over Na₂SO₄ and evaporated.

The product is pure enough ($\geq 97\%$) for the further reaction but can be recrystallized from ethyl acetate/petroleum ether.

Yield: 354 g (97% of theory)

Melting point: 162° C. $[\alpha]_D^{20} = -44.8°$ (CHCl₃)

Example 9

N-Benzyl-4,6-O-isopropylidene-1,2,3,5-tetradeoxy-1,5-imino-D-erythro-2-hexenitol

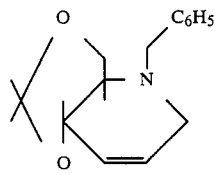

90 g (0.2 mol) of the product from Example 8 are dissolved in 1,600 ml of dimethylformamide and, after addition of 149.9 g (1.0 mol) of NaI and 130.8 g (2.0 mol) of Zn powder, the mixture is stirred at 135° C. for 3 hours (TLC: toluene/EA 3:1). After cooling, the salts are removed by filtration with suction, and the total batch is evaporated, the residue is taken up in CH₂Cl₂, and the solution is washed several times with water. The organic phase is dried over Na₂SO₄ and evaporated, and the remaining syrup is filtered through silica gel (230–400 mesh; mobile phase: toluene; toluene/acetone 30:1).

Yield: 36.3 g (70% of theory) $[\alpha]_D° = -51.4°$ (CHCl₃)

Example 10

N-Benzyl-4,6-O-isopropylidene-1,5-dideoxy-1,5-imino-D-mannitol

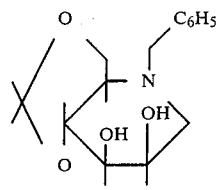

40 g (0.154 mol) of the product from Example 9 are dissolved in 1,200 ml of acetone, 300 ml of H₂O and 100 ml of tert.-butanol and, after addition of 27.0 g (0.2 mol) of N-methylmorpholine N-oxide hydrate and 400 mg of OsO₄, the mixture is stirred until the reaction is found to be complete by thin-layer chromatography (toluene/acetone 1:1). Then 10 ml of cyclohexene are added to the reaction mixture, and stirring is continued for 2 hours (black coloration). The solution is then filtered through Cellite and evaporated. The syrupy residue is taken up in CH₂Cl₂, and the organic phase is washed several times with water, dried over Na₂SO₄ and again evaporated. The residue is purified by flash chromatography on silica gel. (Mobile phase: toluene/ethyl acetate 1:1 to 1.3) and crystallized from ethyl acetate/petroleum ether.

Yield: 33.9 g (75%)

Melting point: 123°–125° C.; $[\alpha]_D^{20} = 122.8°$ (CHCl₃)

Example 11

N-Benzyl-3-O-benzyl-4,6-O-isopropylidene-1,5-dideoxy-1,5-imino-D-mannitol

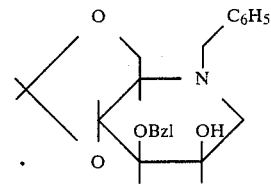

A solution of 15 g (51 mmol) of the compound of Example 10 in 300 ml of absolute toluene, in which 14 g (56 mmol) of dibutyltin oxide are suspended, is heated to reflux under a protective atmosphere of N₂ gas and using a water separator until no more water is observed to separate out. The temperature is then lowered to 100° C., and 1.64 g (5.1 mmol) of tetrabutylammonium bromide are added to the solution under a countercurrent of nitrogen. Thereafter 9.58 g (56 mmol) of benzyl bromide are slowly added dropwise over the course of 5 hours. After 8 hours it is established by thin-layer chromatography (system toluene:acetone=5:1) that the precursor has almost completely reacted, and working up is carried out. This is effected by removal of the solvent by evaporation, taking up the residue in chloroform, and subsequently washing the organic phase with saturated sodium bicarbonate solution. Tin salts resulting from this are removed by centrifugation. The crude product obtained after drying over sodium sulphate and removal of the solvent by evaporation is freed of concomitant byproducts by column chromatography in the system toluene:acetone=40:1.

Yield: 14.3 g (37 mmol; 73% of theory)

$[\alpha]_D^{20} = -55.3°$; C=0.85; (ethanol)

Example 12

N-Benzyl-3-O-benzyl-4,6-O-isopropylidene-2-trifluoromethanesulphonyl-1,5-dideoxy-1,5-imino-D-mannitol

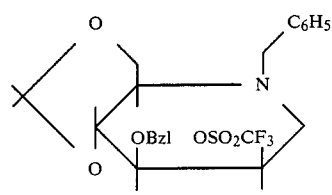

14 g (37 mmol) of the compound of Example 11 are dissolved in 140 ml of absolute dichloromethane. 6.9 g (88 mmol) of pyridine are added to the solution which is maintained at a constant temperature of −20° C. under an inert gas atmosphere. Under these conditions, 10.4 g (37 mmol) of trifluoromethanesulphonic anhydride, dissolved in 60 ml of absolute dichloromethane, are added dropwise over 60 min. After a reaction time of 1 hour the starting material has been converted into final product. ($R_f=0.3$, toluene:acetone=10:1).

The working up is carried out by addition of 50 ml of saturated sodium bicarbonate solution. After vigorous stirring at 0° C. for 30 minutes, the organic phase is dried over sodium sulphate and evaporated. 18.1 g (35 mmol; 95%) of product are obtained, and this is immediately subjected to the next reaction step.

Example 13

2-Azido-N-benzyl-3-O-benzyl-4,6-O-isopropylidene-1,2,5-trideoxy-1,5-imino-D-glucitol

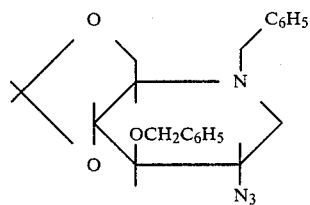

18.1 g (35 mmol) of the compound from Example 12 are dissolved in 40 ml of absolute dichloromethane under a protective gas atmosphere. The temperature is kept constant at −40° C. and 100 ml of absolute dimethylformamide are slowly added. Then 8.6 g (0.175 mol) of lithium azide are added. The mixture is stirred at −40° C. under protective gas. After about 8 hours, precursor is no longer detectable by thin-layer chromatography (Spray reagent: naphthoresorcinol).

Figure 1:
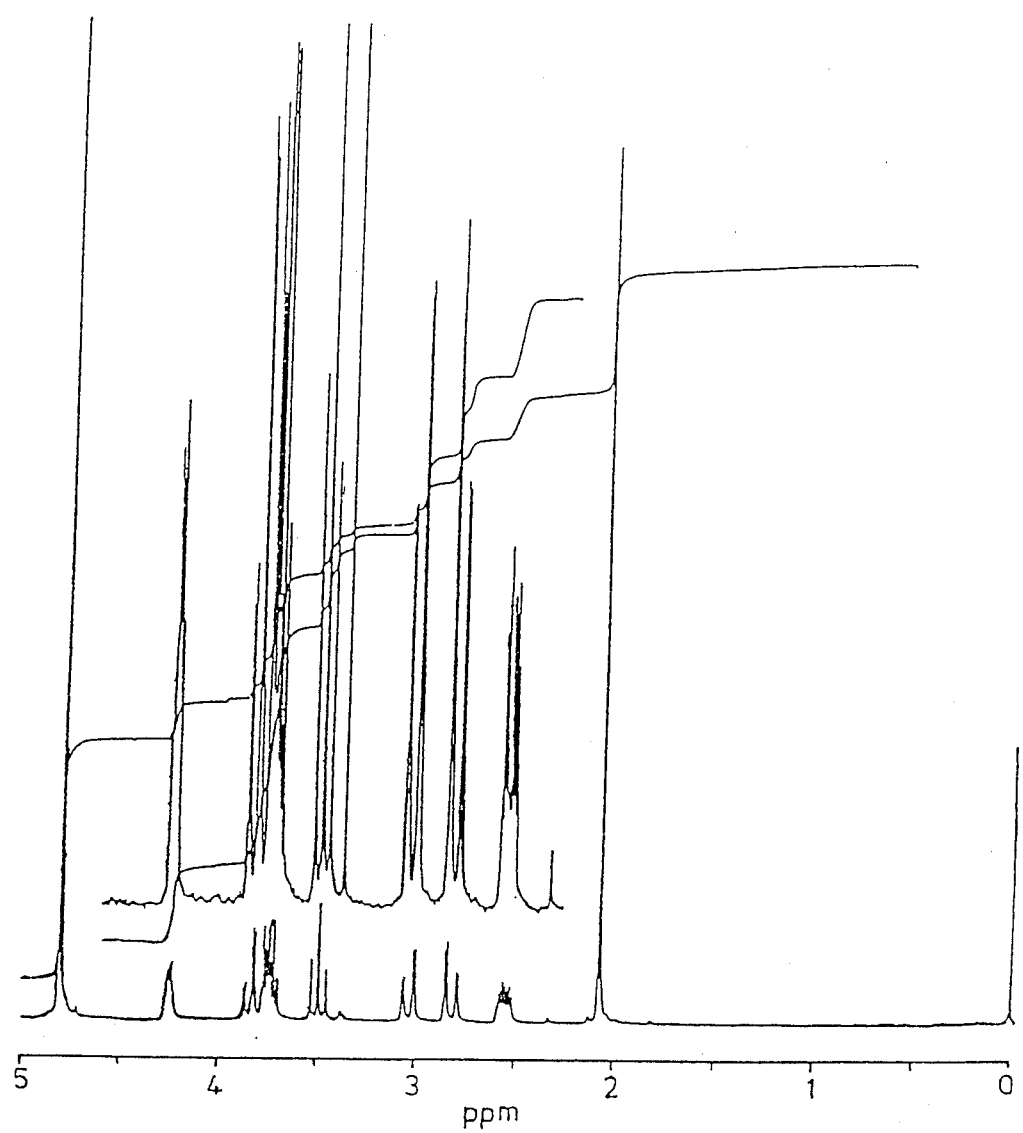
Figure 2:
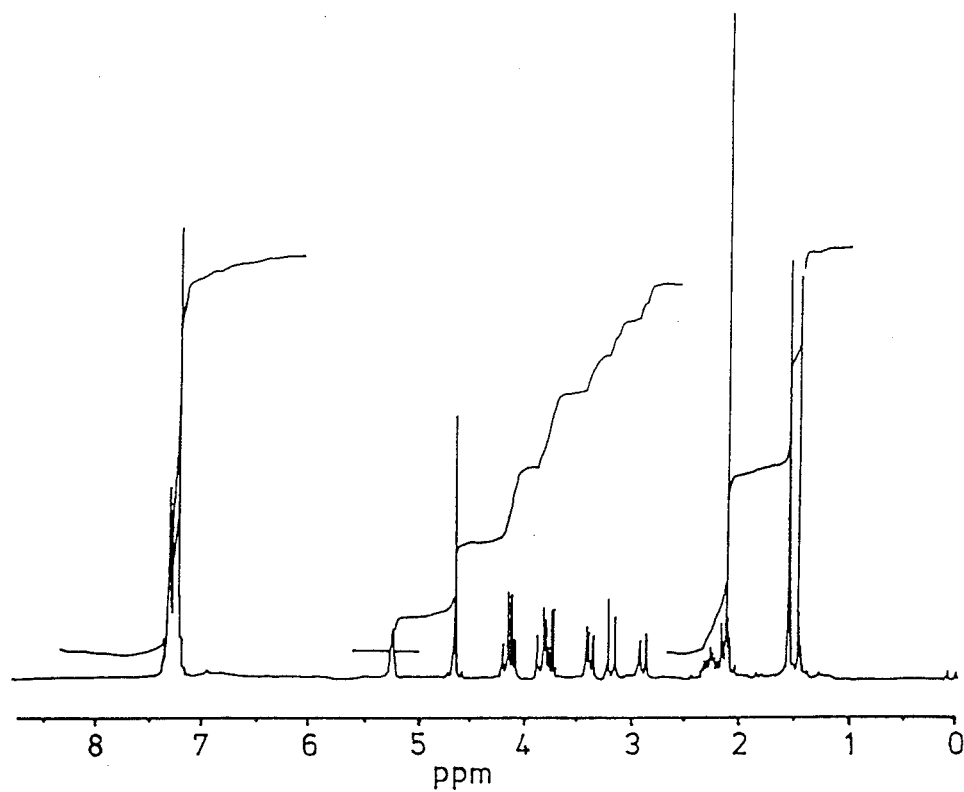
FIG. 2 shows the ¹H NMR spectrum of the compound of Example 11 (200 MHz, CDCl₃)
Figure 3:
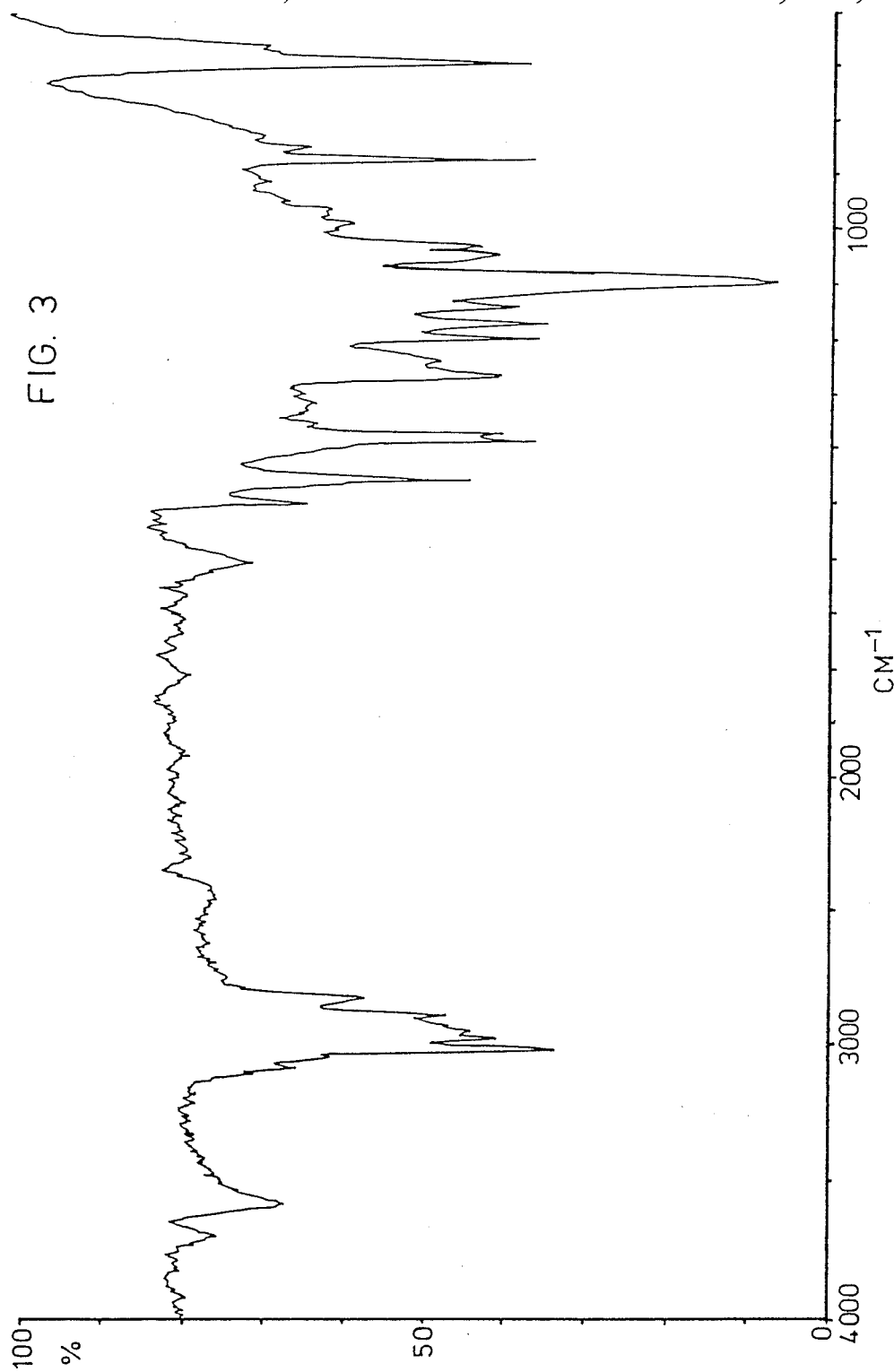
FIG. 3 shows the IR spectrum of the compound of Example 11 (CHCl₃)
Figure 4A:
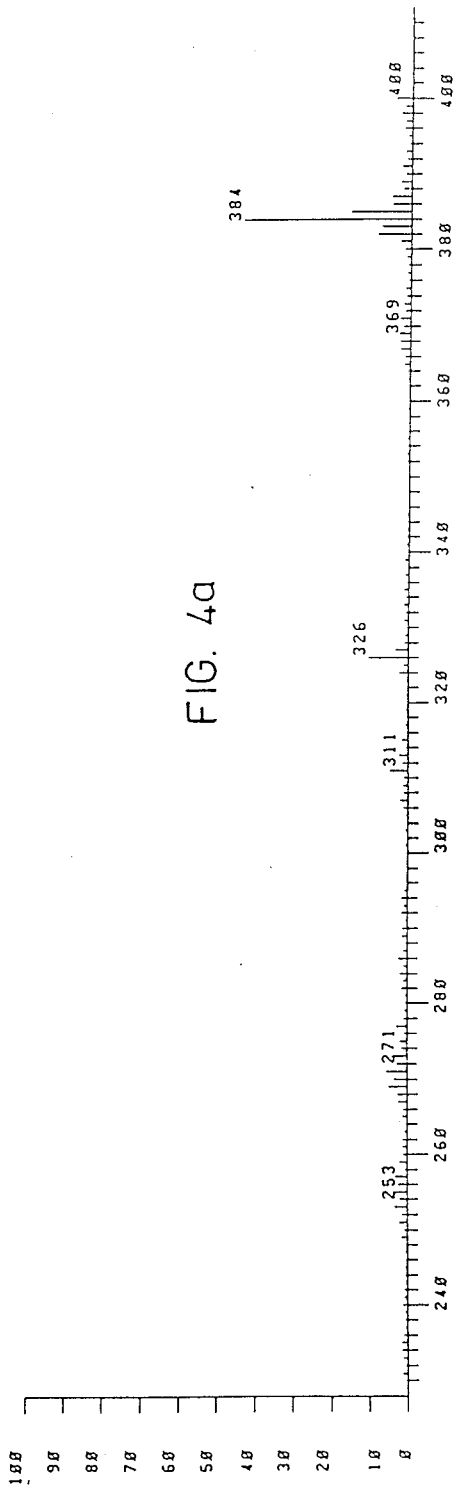
FIG. 4 shows the mass spectrum of the compound of Example 11
Figure 4B:
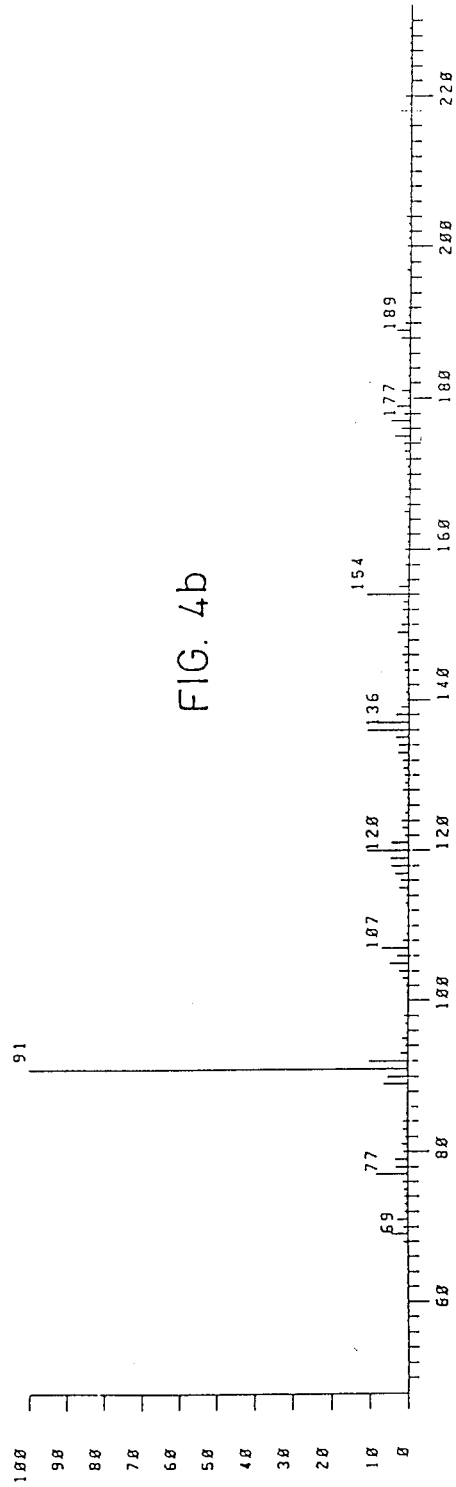
Figure 5:
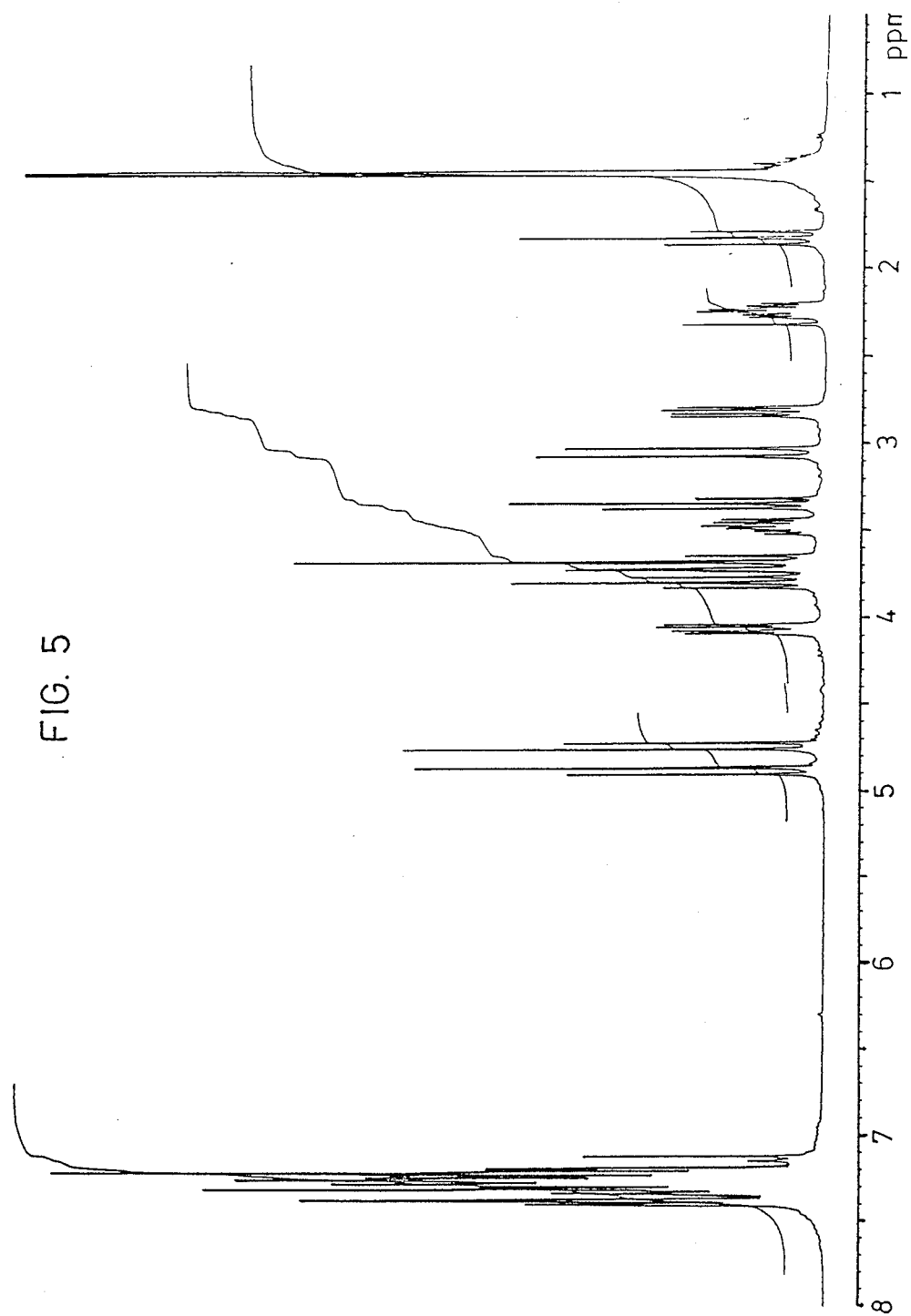

The working up is carried out by evaporation at a bath temperature of 30° C. under high vacuum to about ¾ of the initial volume, taking up the residue in toluene, and washing the solution several times with dilute NaCl solution. After drying over sodium sulphate and purification of the product by column chromatography in the system toluene:ethyl acetate=50:1, 10.6 g (26.5 mmol; 74%) of the crude product are obtained. $[\alpha]_D^{20}=-78.86°$ FIG. 5 shows the ¹H NMR spectrum of the compound of Example 13 (300 MHz, CDCl₃).

Figure 6:
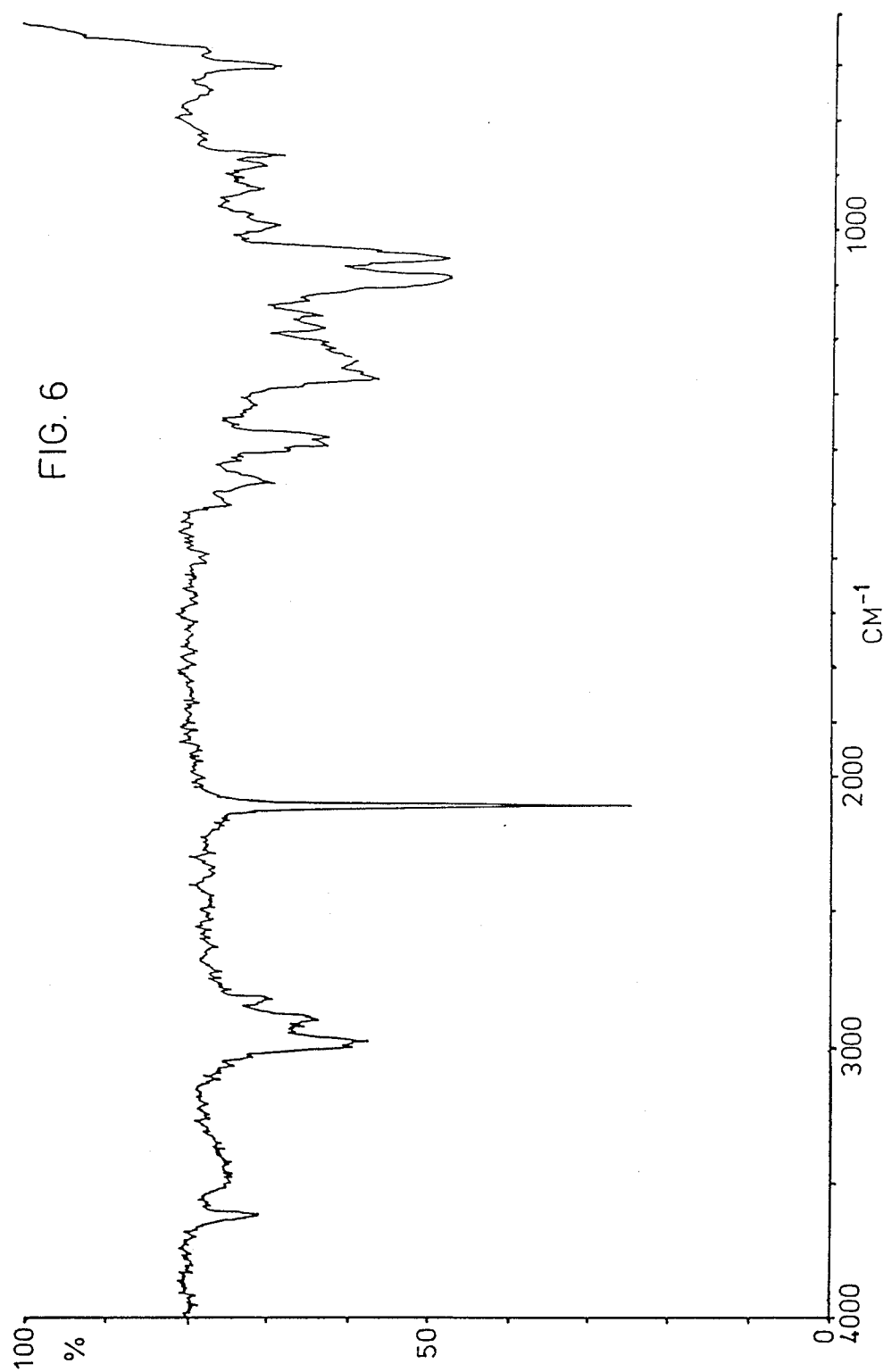

FIG. 6 shows the IR spectrum of the compound of Example 13 (CHCl₃).

Example 14 and 15

2-Amino-N-benzyl-3-O-benzyl-4,6-isopropylidene-1,2,5-trideoxy-1,5-imino-D-glucitol 14 and 2-acetamido-N-benzyl-3-O-benzyl-4,6-isopropylidene-1,2,5-trideoxy-1,5-imino-D-glucitol 15

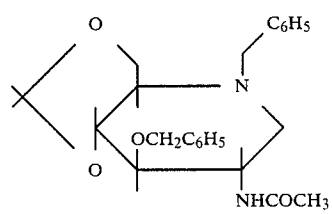

10.6 g (26 mmol) of the compound of Example 13 are taken up in 100 ml of a 4% ethanolic NiCl₂ solution and, while stirring at 0° C., a saturated ethanolic solution of NaBH₄ is added until the initially reversible black coloration persists. A check by thin-layer chromatography (tol:ethanol=10:1) then shows that the precursor has been completely converted into the 2-amino compound 14. (Ninhydrin visualization: red coloration). Working up is carried out by evaporating off the solvent in a rotary evaporator at a bath temperature of 30° C. under high vacuum and subsequent in situ acetylation by taking up in 50 ml of acetylation mixture composed of acetic anhydride:pyridine=1:2. After a reaction time of 2 hours at 40° C., 14 has been completely transformed into 15 (Product no longer gives red color with ninhydrin). The mixture is evaporated to dryness under high vacuum, and the residue is taken up in toluene/H₂O.

Nickel and boron salts are removed by extraction several times with semi-saturated NaCl solution, and the toluene phase is dried over sodium sulphate and evaporated, and the product is chromatographed on silica gel in the system toluene:ethanol=60:1.

Yield: 9.6 g (87%) of 15
$[\alpha]_D^{20}=-3.3°$ (CHCl₃)
Melting point: 40° C.

Figure 7:
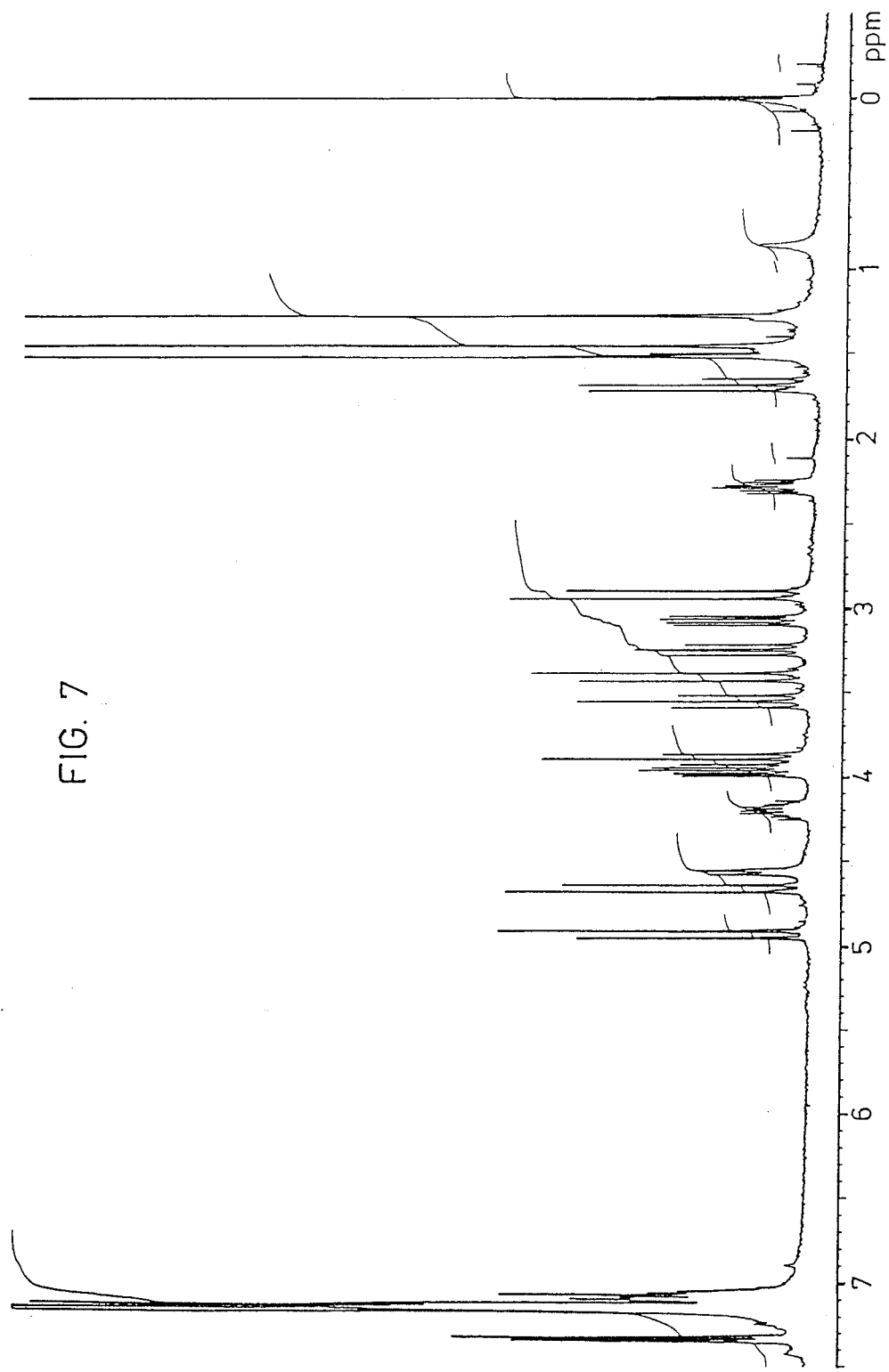

FIG. 7 shows the ¹H NMR spectrum of the compound of Example 15 (300 MHz, C₆D₆)

Figure 8:
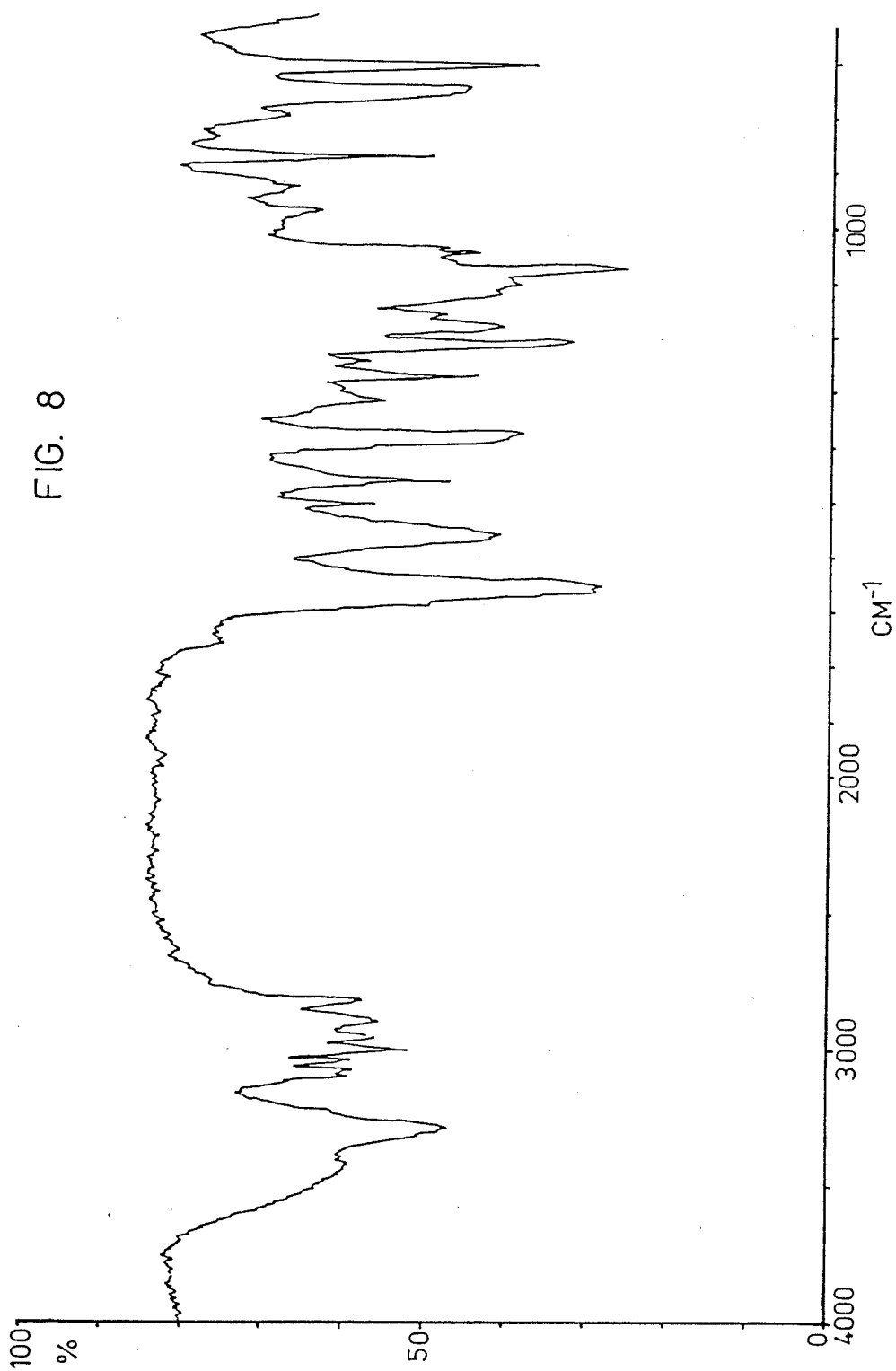

FIG. 8 shows the IR spectrum of the compound of Example 15 (KBr)

Figure 9A:
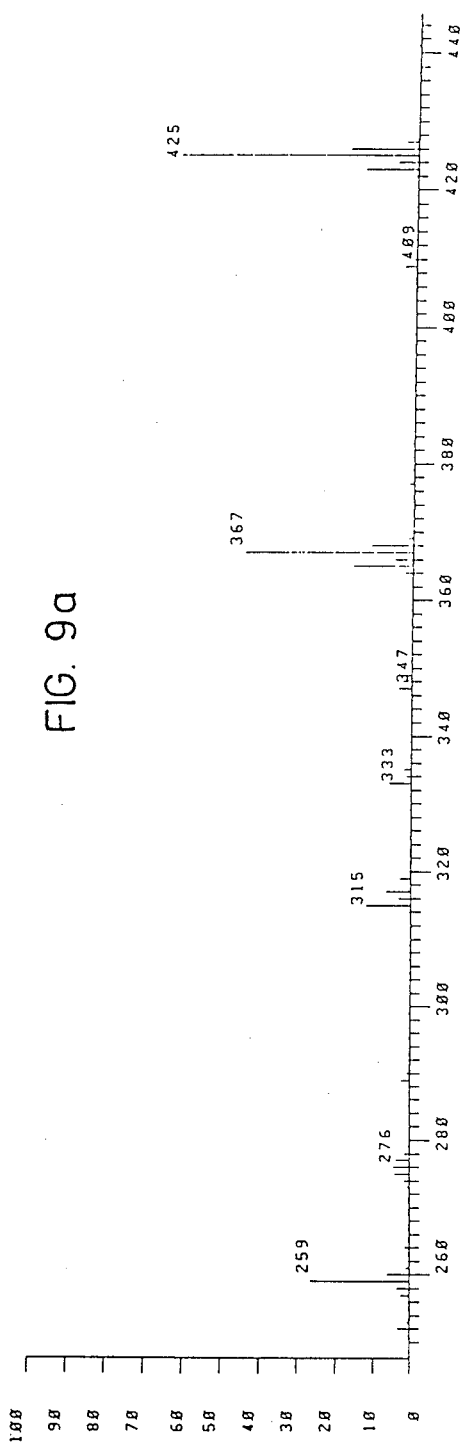
Figure 9B:
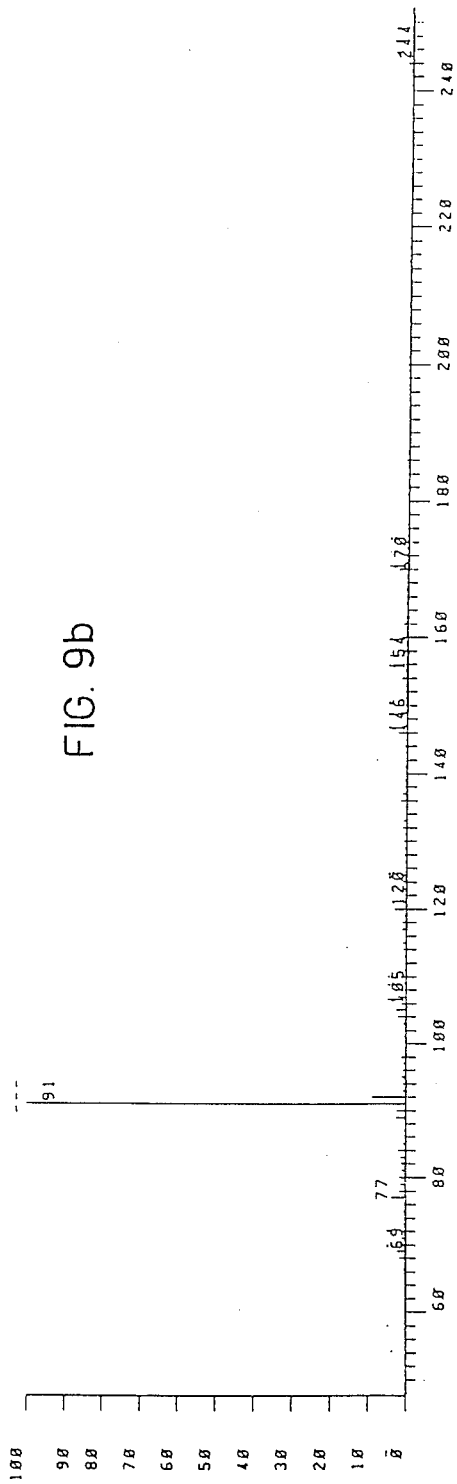

FIG. 9 shows the mass spectrum of the compound of Example 15

Example 16

2-Acetamido-4,6-O-isopropylidene-1,2,5-trideoxy-1,5-imino-D-glucitol acetic acid salt

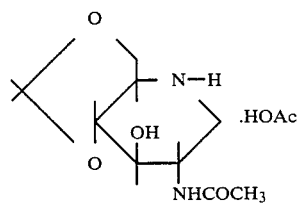

2 g (15 mmol) of the compound of example 15, in 50 ml of methanol to which 2 ml of glacial acetic acid and 5 g of 10% palladium/charcoal are added, are hydrogenated under 3 bar for 24 hours. Compound 15 is converted quantitatively into the acetic acid salt of the final product, from which the final product is obtained pure by evaporation with triethylamine several times.

Yield: 1.1 g (quantitative)

Melting point: of the acetic acid salt: 166°–169° C. decomposition $[\alpha]_D^{20}$ of the acetic acid salt$=-4.35°$ (pyridine, C=0.58)

Figure 10:
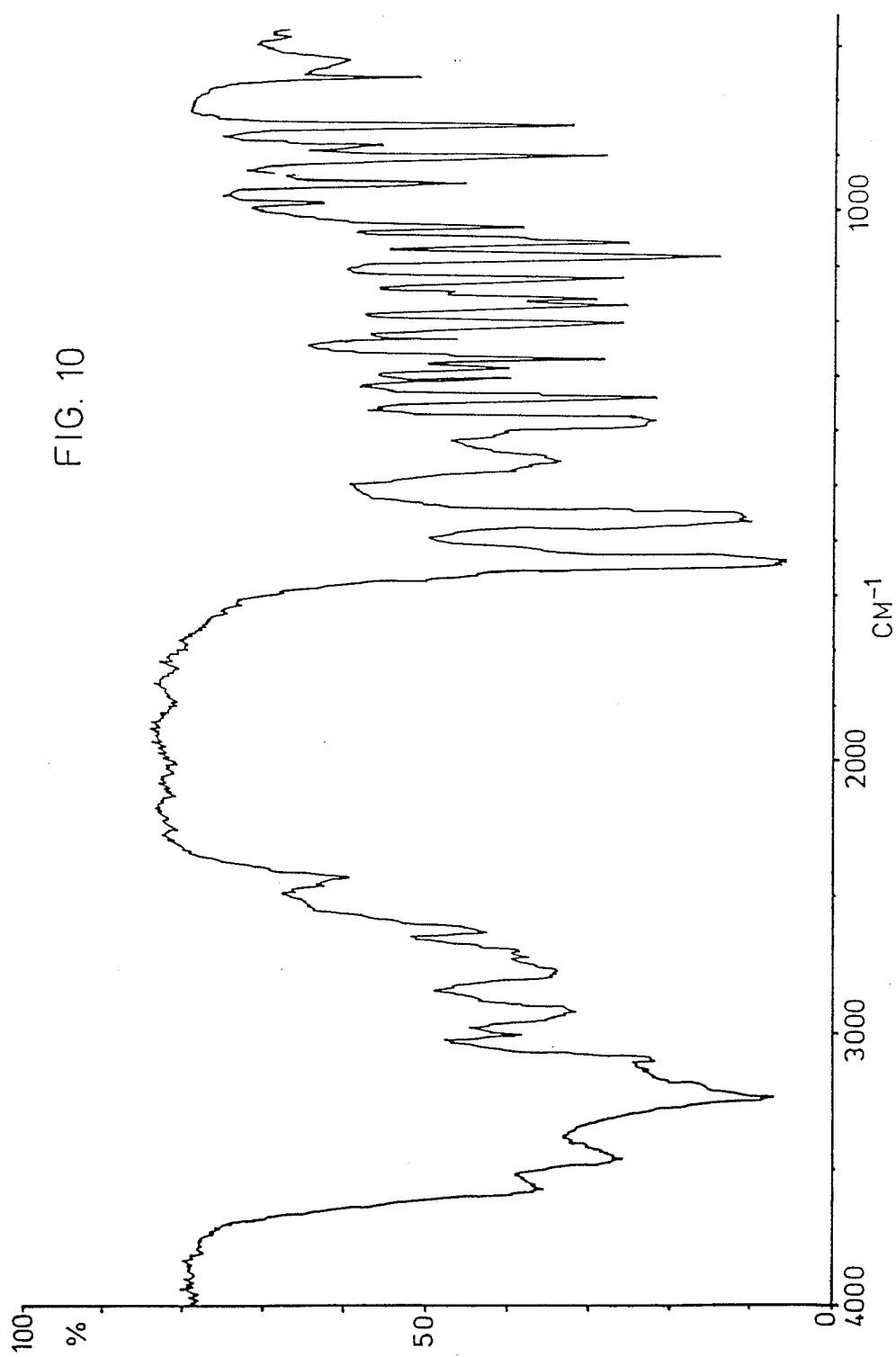

FIG. 10 shows the IR spectrum of the compound of Example 16 (KBr)

Figure 11A:
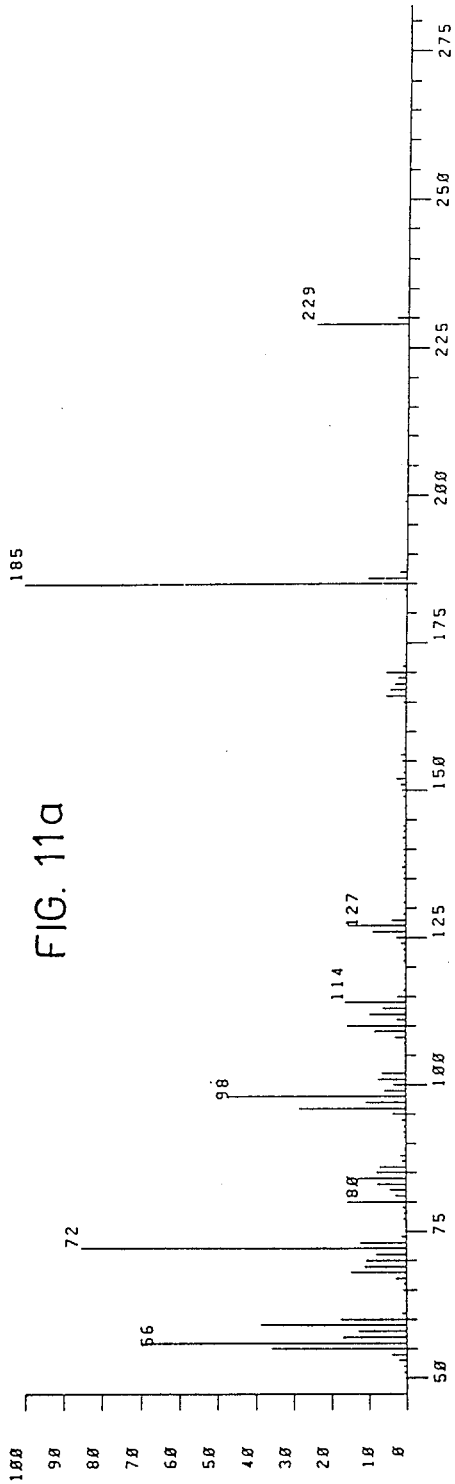
Figure 11B:
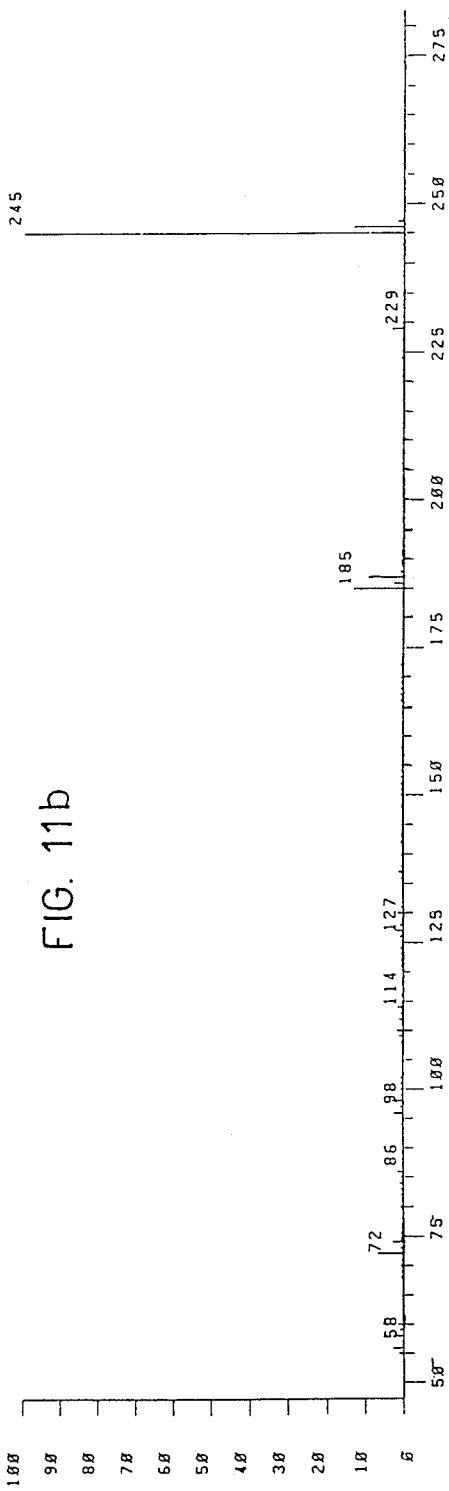

FIG. 11 shows the mass spectrum of the compound of Example 16.

Example 17

2-Acetamido-1,2-dideoxy-nojirimycin

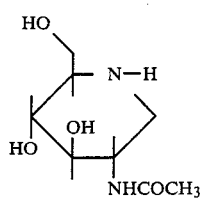

1.1 g of the compound of Example 16 (5 mmol) are dissolved in 20 ml of a mixture of glacial acetic acid: $H^2O=3:2$, and the solution is heated at 60° C. for 8 hours. After the hydrolysis mixture has been evaporated, the product is dried and evaporated several times with methanol/triethylamine and the final product is obtained in quantitative yield.

$[\alpha]_D^{20}=+9.9°$ (H$_2$O)

Melting point: 220.5°–221.7° C.

Figure 12:
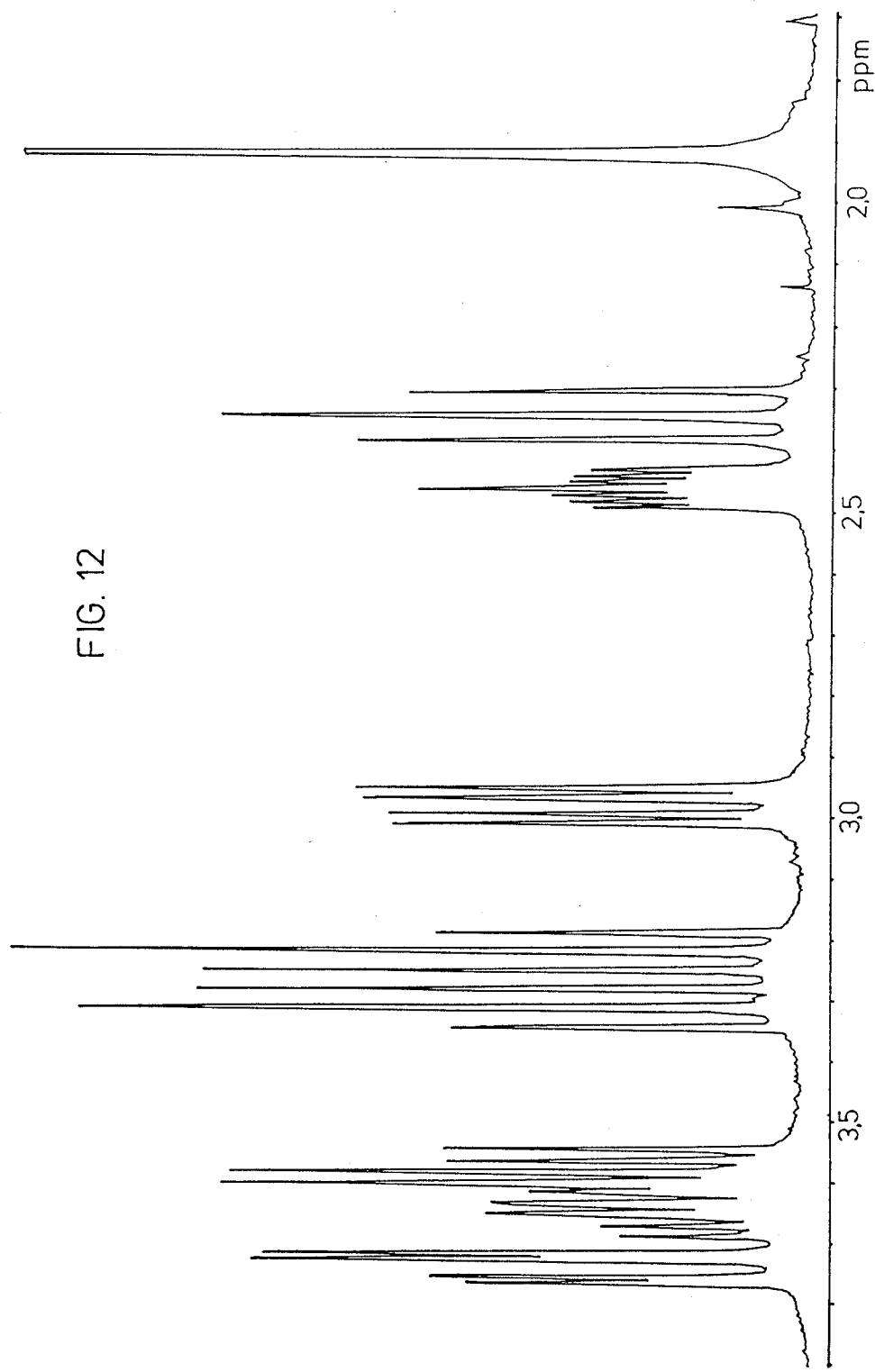

FIG. 12 shows the $^1$H NMR spectrum of the compound of Example 17 (300 MHz, D$_2$O)

Figure 13:
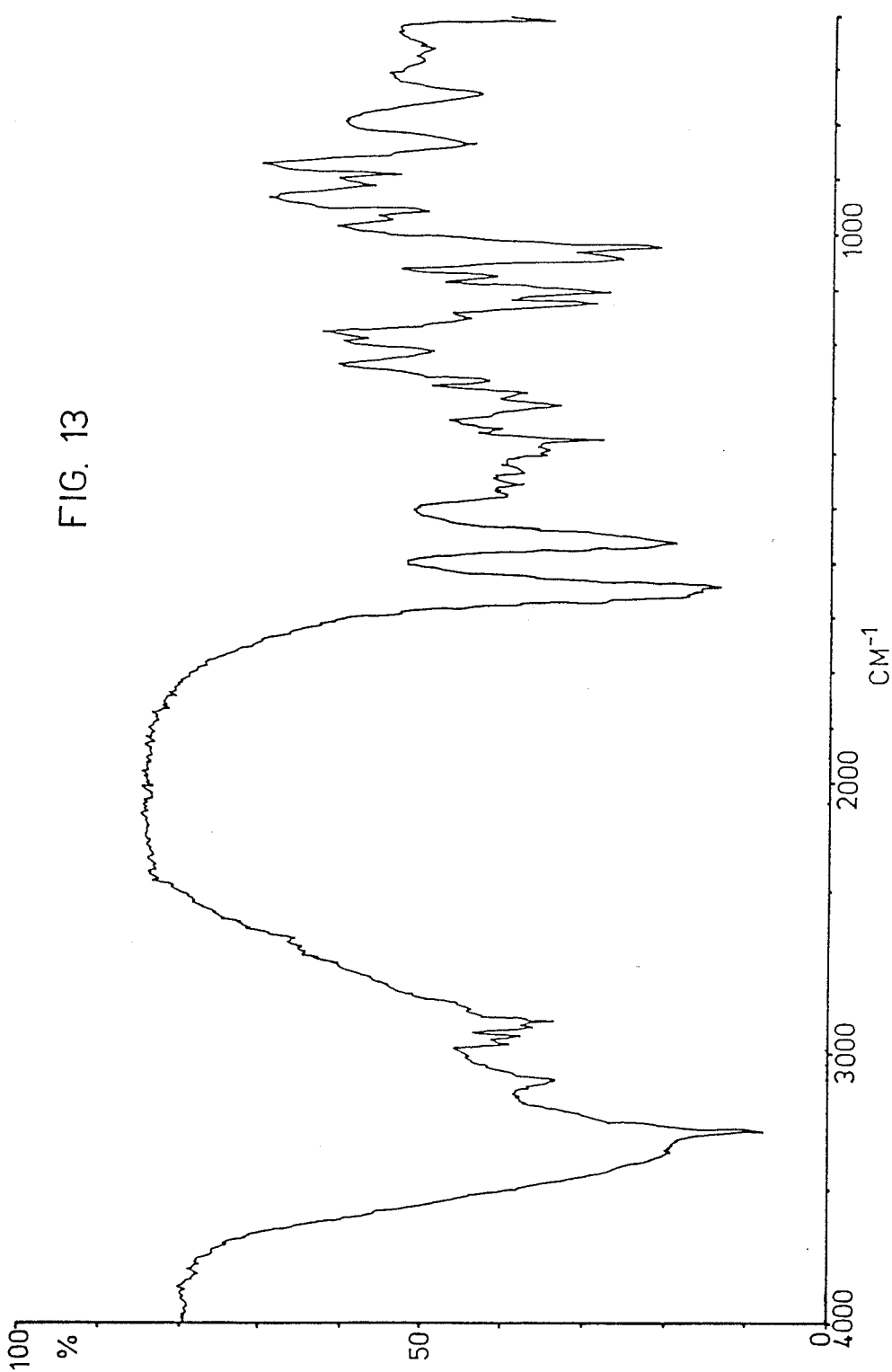

FIG. 13 shows the IR spectrum of the compound of Example 17 (KBr)

Figure 14:
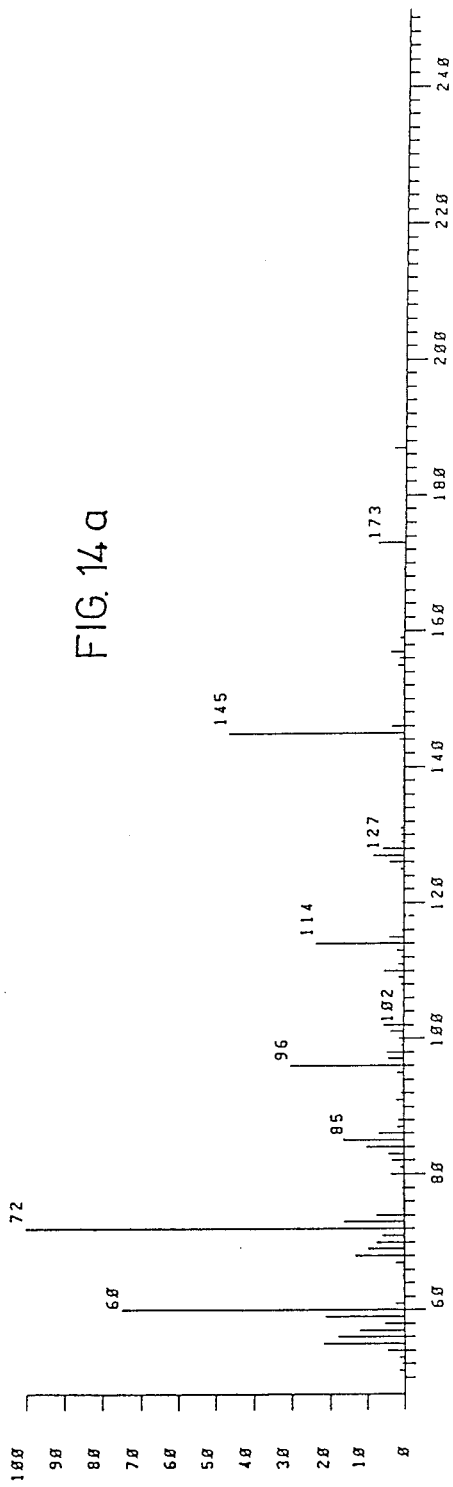
Figure 14:
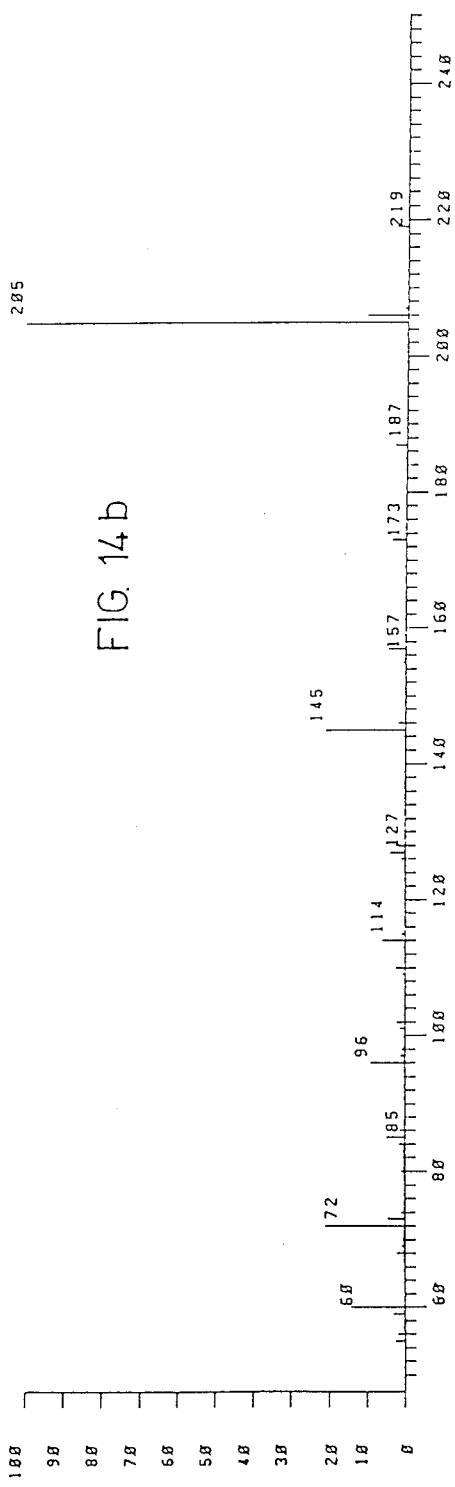

FIG. 14 shows the mass spectrum of the compound of Example 17

Example 18

N-Benzyl-3-O-p-methoxybenzyl-4,6-O-isopropylidene-1,5-dideoxy-1,5-imino-D-mannitol

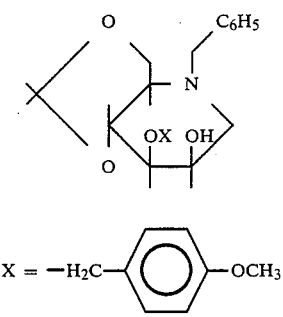

A solution of 58.6 g of the compound of Example 10 in 700 ml of absolute toluene, in which 55 g of dibutyltin oxide are suspended, is heated to reflux under a protective atmosphere of N$_2$ gas and using a water separator until no more water is found to separate out. The temperature is then lowered to 100° C. and, with a counter-current of nitrogen, 6 g of tetrabutylammonium bromide are added. Thereafter 34.5 g of p-methoxybenzyl chloride are slowly added dropwise over the course of 5 hours. After 12 h it is established by thin-layer chromatography (system toluene:acetone=4:1) that the precursor has reacted completely. Working up is carried out by evaporating off the solvent, taking up the residue in chloroform and subsequently washing the organic phase with saturated sodium bicarbonate solution. Tin salts resulting from this are removed by centrifugation. The crude product obtained after drying over sodium sulphate and evaporating off the solvent is freed of concomitant byproducts by column chromatography in the system toluene:acetone=40:1. After crystallization from ethyl acetate/hexane=36 g of the title compound are obtained.

Melting point: 88° C.

$[\alpha]_D^{20}=-70.9°$ (chloroform C=0.98)

Figure 15:
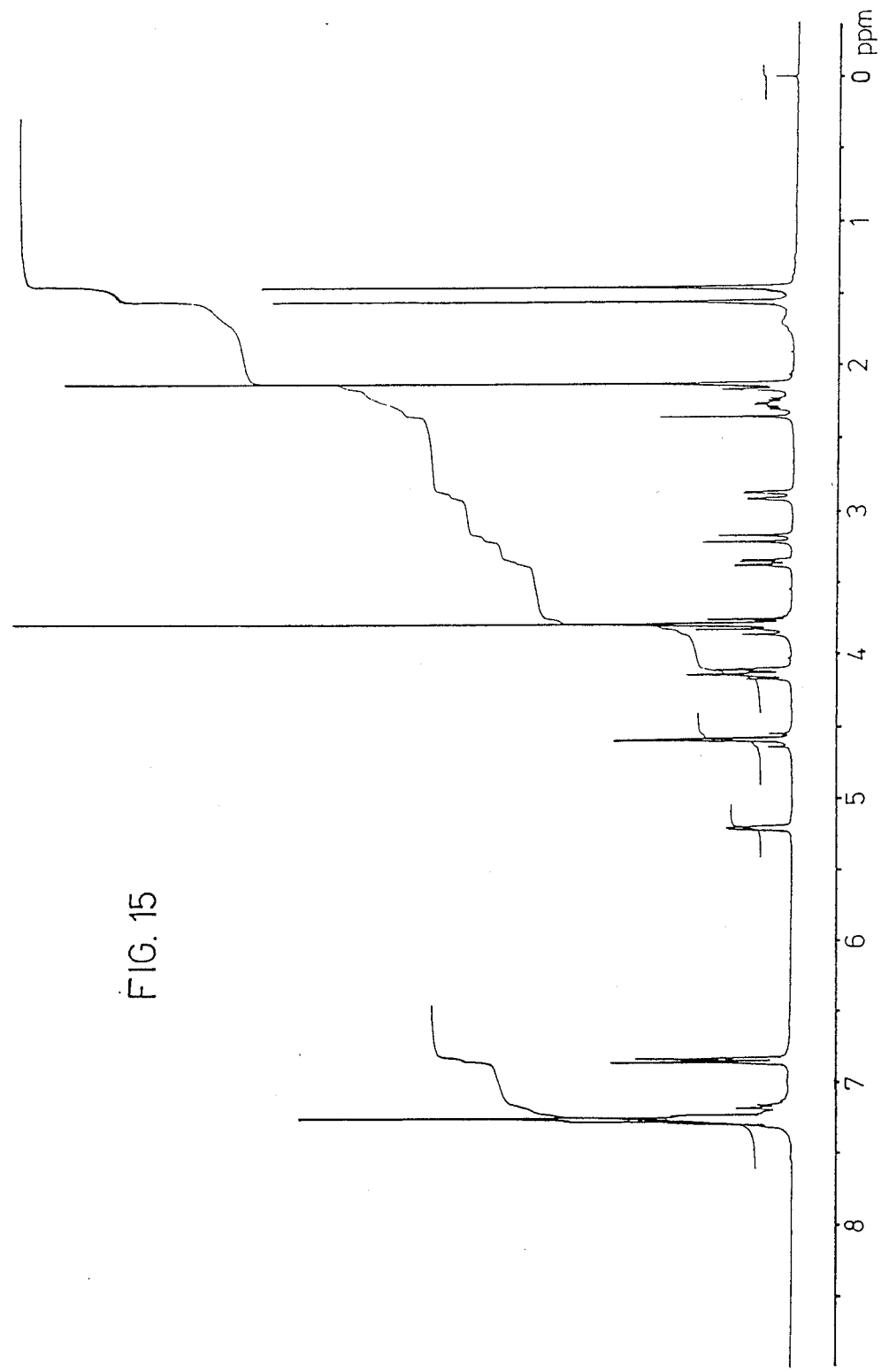

FIG. 15 shows the $^1$H NMR spectrum of the compound of Example 18 (300 MHz, CDCl$_3$)

Figure 16:
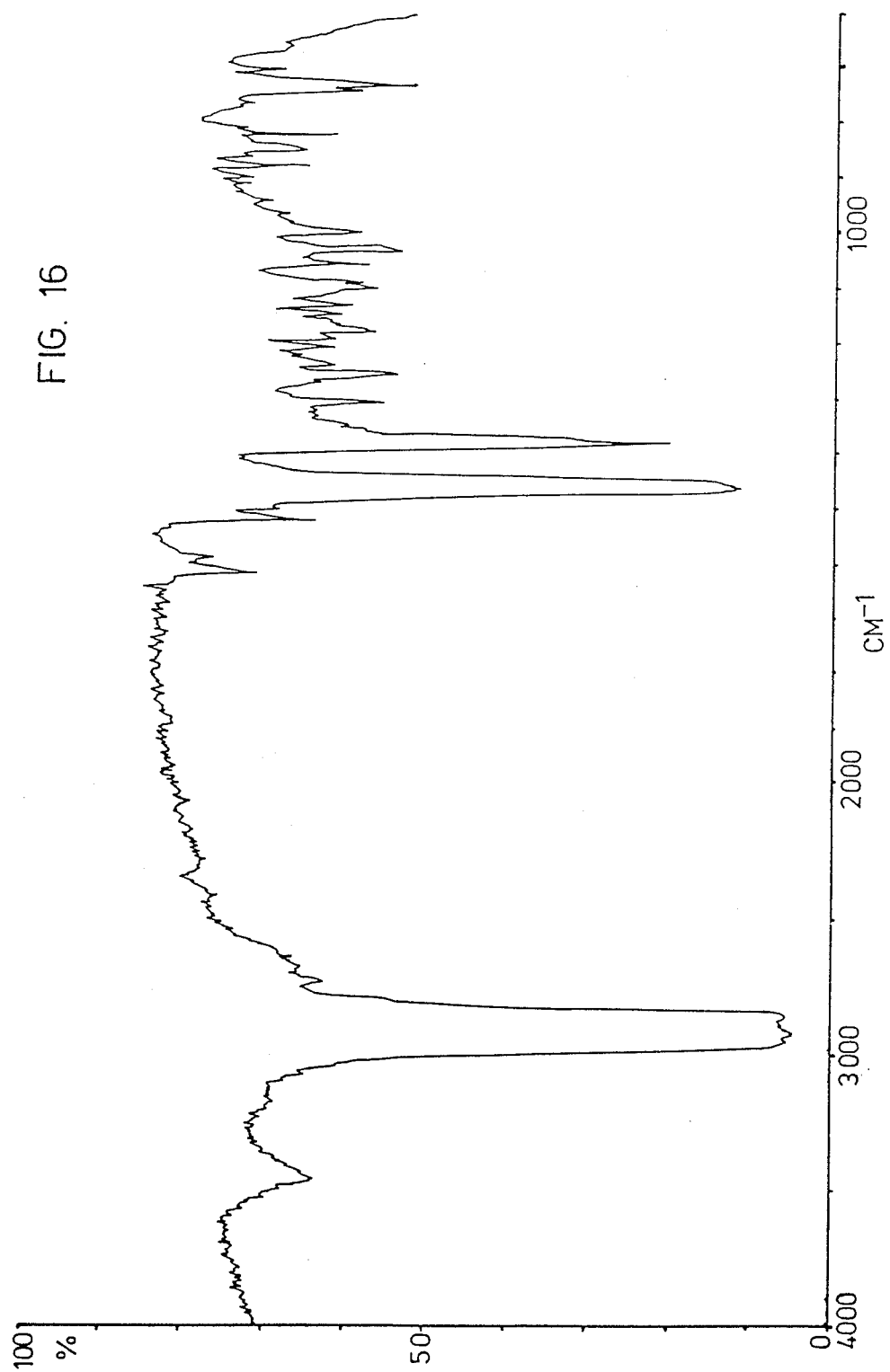

FIG. 16 shows the IR spectrum of the compound of Example 18 (nujol)

Figure 17A:
Figure 17B:
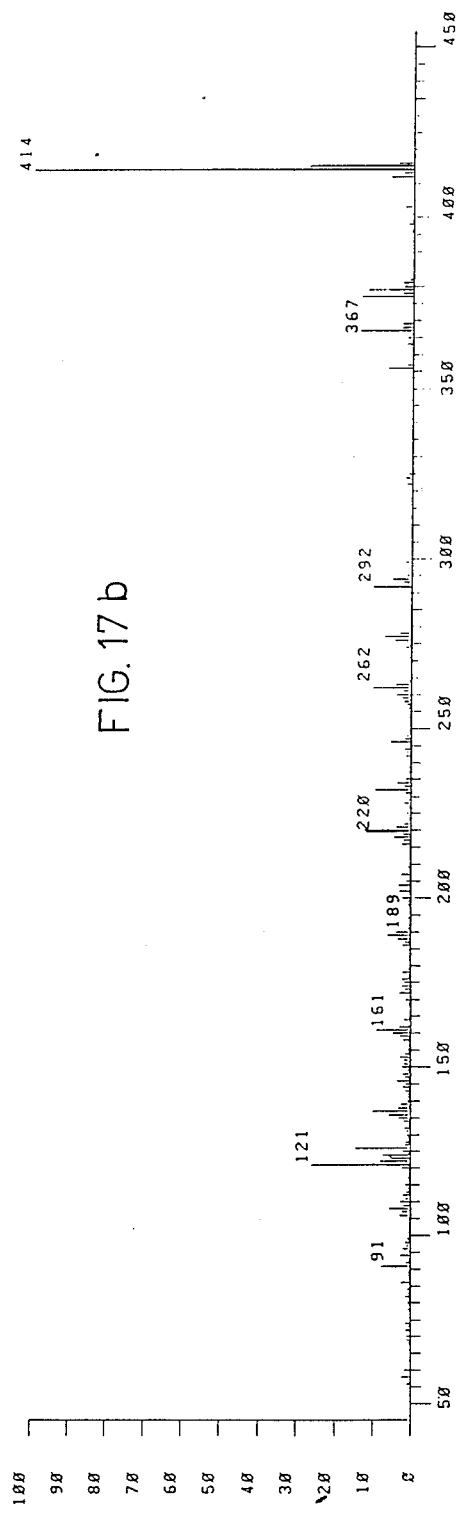

FIG. 17 shows the mass spectrum of the compound of Example 18

Example 19

2-Acetamido-N-benzyl-1,2-dideoxy-nojirimycin

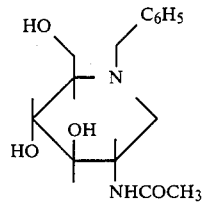

1 g (5.3 mmol) of the compound of Example 17 are dissolved in 20 ml of dimethylformamide in which 1.6 g (11.6 mmol) of potassium carbonate are suspended by stirring. 900 mg (5.3 mmol) of benzyl bromide are added to the mixture at 0° C. The reaction is complete after 8 hours. The sediment is removed by filtration, and the product is isolated in quantitative yield after evaporation of the solvent.

$R_f=0.3$ (CHCl$_3$:MeOH=4:1)

$[\alpha]_D^{20}$ of the acetic acid salt$=+25.0°$ (H$_2$O; C=1.41)

Figure 18:
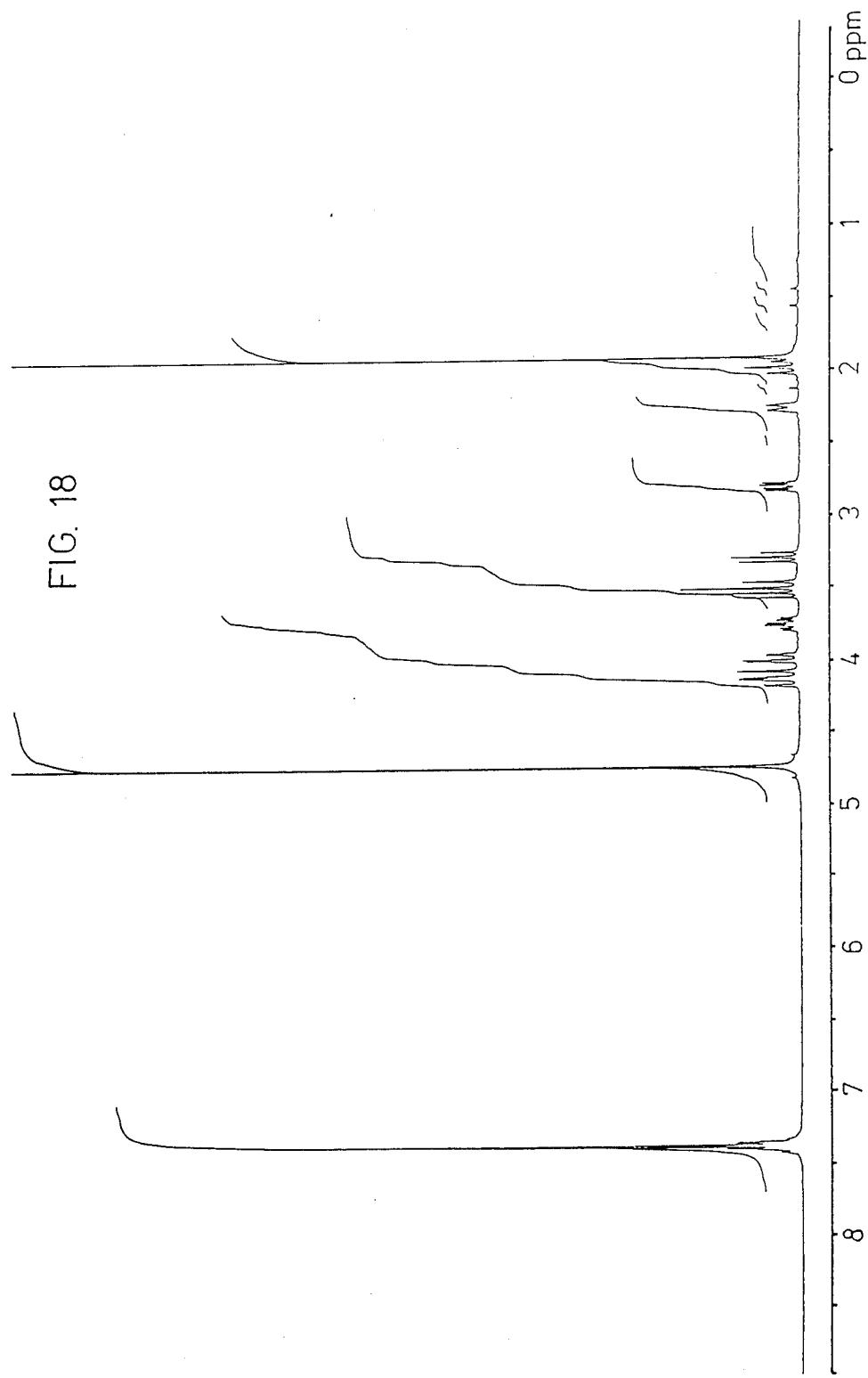

FIG. 18 shows the $^1$H NMR spectrum of the compound of Example 19 (300 MHz, D$_2$O).

Figure 19:
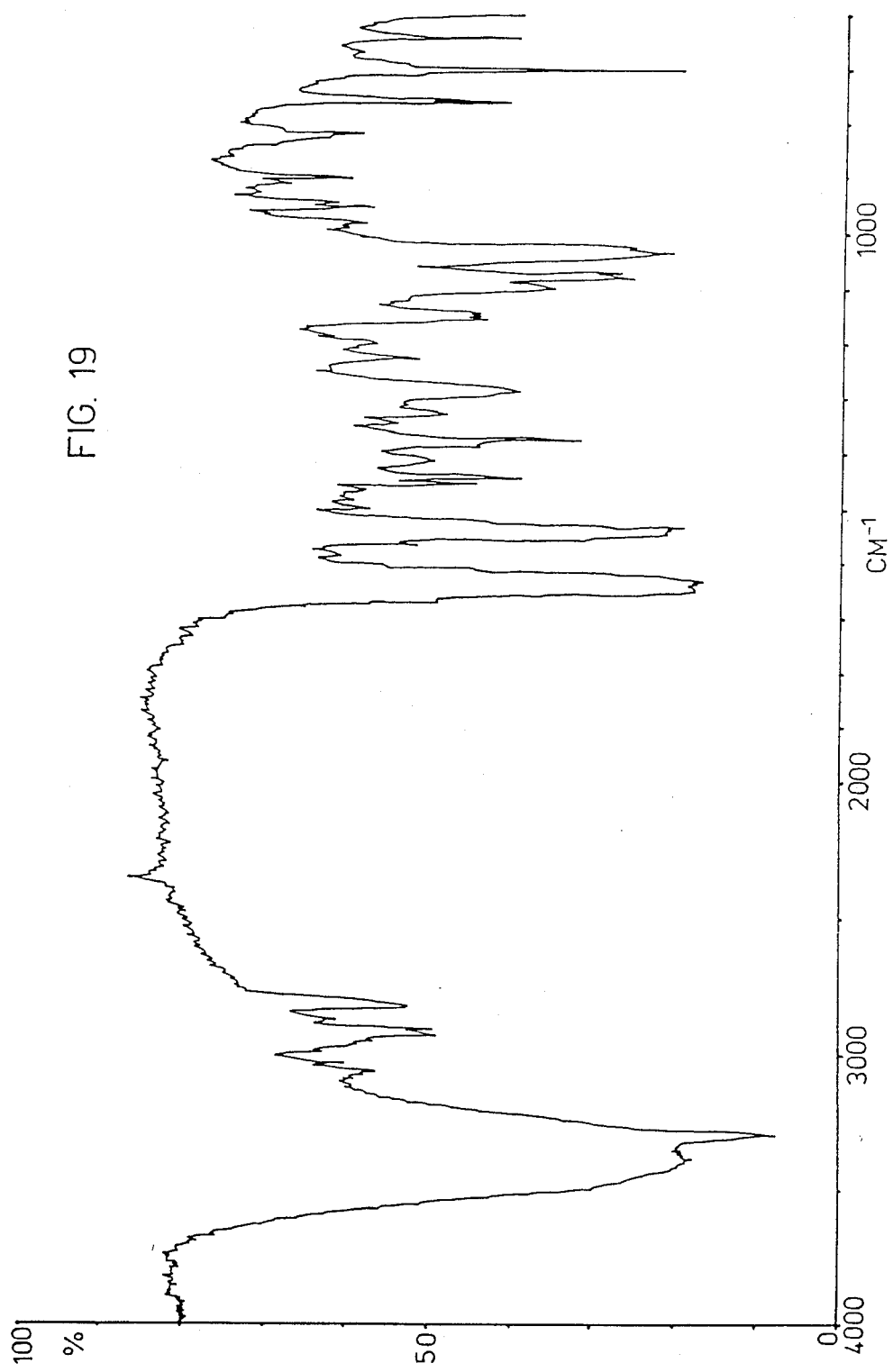

FIG. 19 shows the IR spectrum of the compound of Example 19 (KBr).

Example 20

2-Acetamido-N-methyl-1,2-dideoxy-nojirimycin

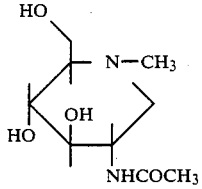

1 g (5.3 mmol) of the compound of Example 17 are dissolved in 30 ml of a mixture of methanoic acid and methanol in the ratio 2:1 (V/V), and the solution is heated at 80° C. for 12 hours. The residue isolated after the solvent has been evaporated off is taken up in methanol, and salts are removed on an Amberlit type CG 4001 basic ion exchanger.

Yield: quantitative.

$R_f=0.44$ (system $CHCl_3:MeOH:NH_3H_2O=4:3:1$)

$[\alpha]_D^{20}=+10.72°$

Figure 20:
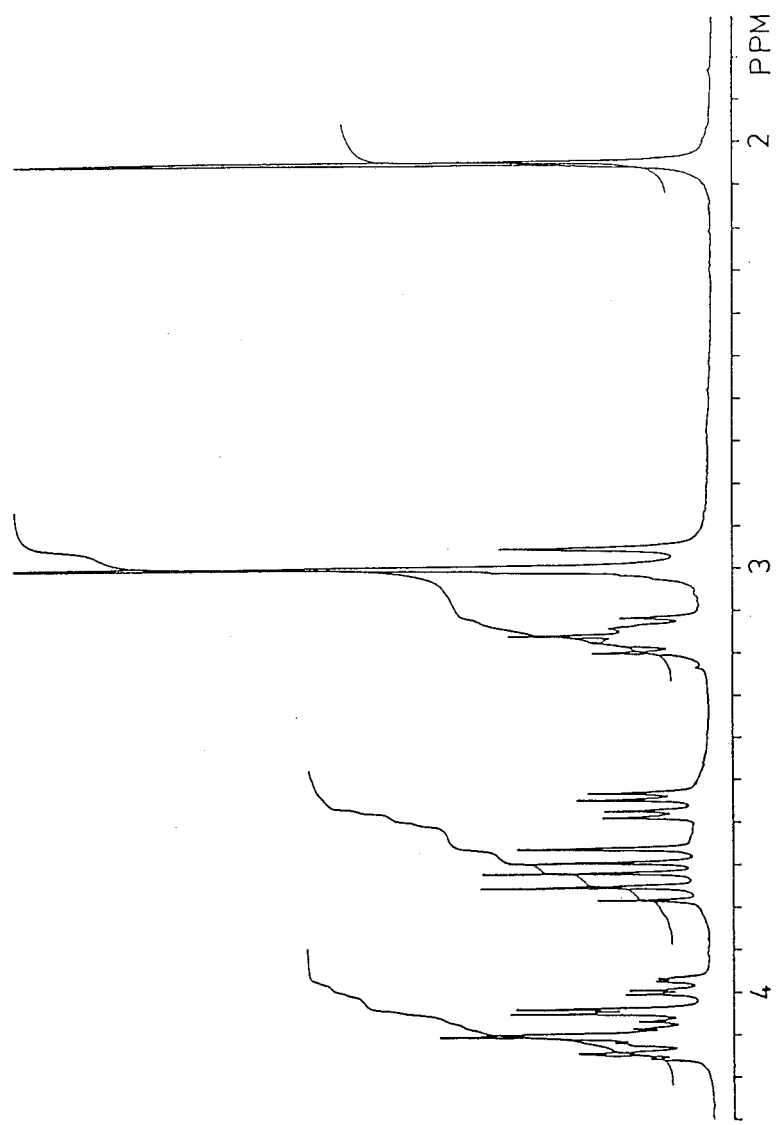

FIG. 20 shows the $^1H$ NMR spectrum of the compound of Example 20 (300 MHz, $D_2O$)

Figure 21:
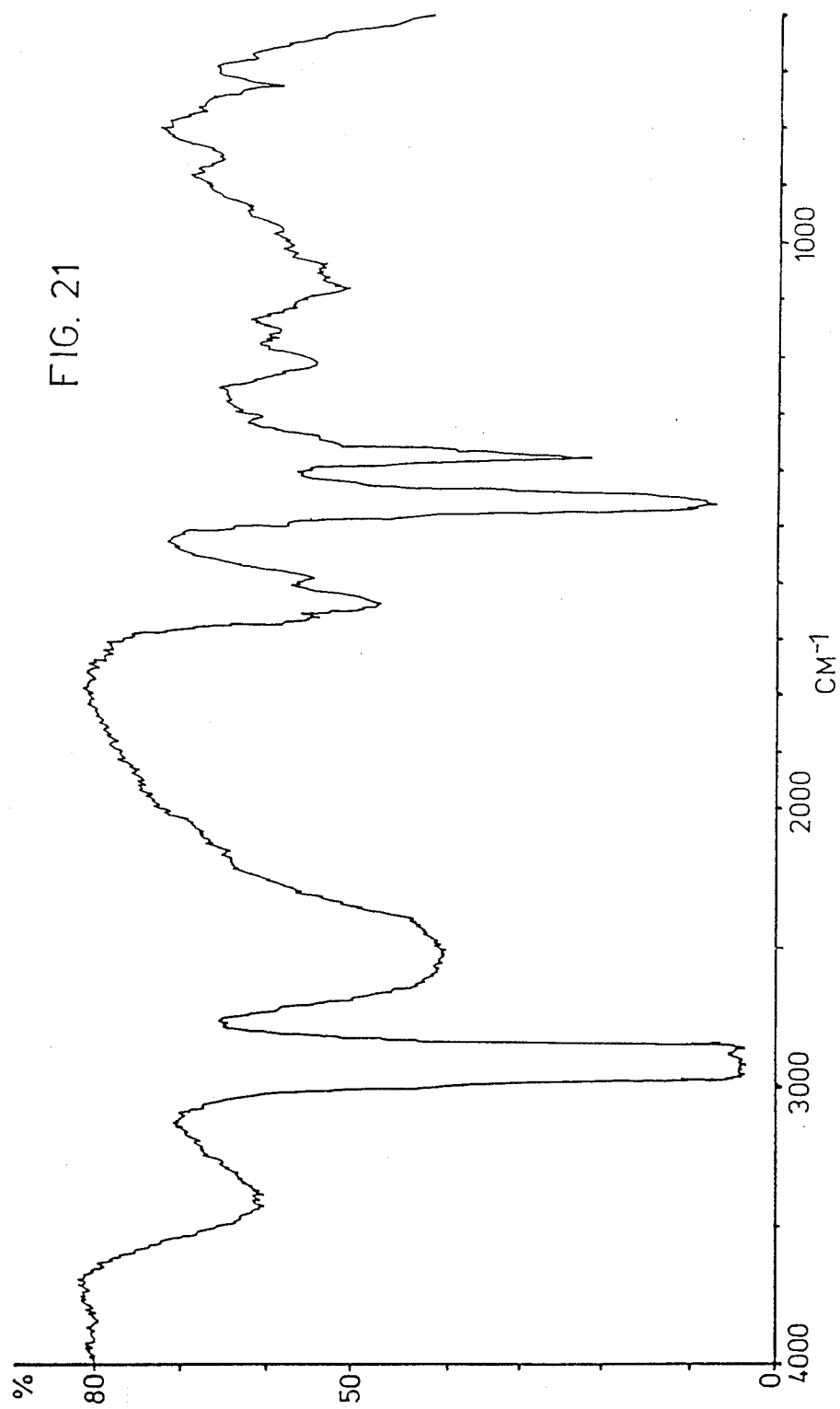

FIG. 21 shows the IR spectrum of the compound of Example 20 (KBr).

It will be appreciated that the instant specification and claims are set forth by way of illustration and not limitation, and that various modifications and changes may be made without departing from the spirit and scope of the present invention.

We claim:

1. A 3-amino-4,5-dihydroxypiperidine of the formula

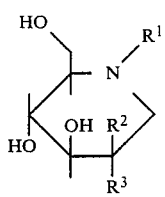 (I)

in which

R$^1$ represents hydrogen, alkyl having up to 8 carbon atoms, aralkyl having 7 to 14 carbon atoms, or represents a group of the formula

R$^4$ denotes straight-chain or branched alkyl having up to 8 carbon atoms, straight-chain or branched alkoxy having up to 8 carbon atoms, or aralkoxy having up to 10 carbon atoms, and R$^2$ and R$^3$ represent hydrogen or represent the group NHR$^5$, R$^5$ having the same meaning as R$^1$ and being identical to or different from the latter, with the proviso that, in every case, one substituent of R$^2$ or R$^3$ represents hydrogen and the other substituent of R$^2$ or R$^3$ represents NHR$^5$, and physiologically acceptable salts thereof.

2. A 3-amino-4,5-dihydroxypiperidine according to claim 1,
in which
R$^1$ represents hydrogen or alkyl having up to 6 carbon atoms, or R$^1$ represents benzyl or represents a group of the formula

in which
R$^4$ denotes straight-chain or branched alkyl having up to 4 carbon atoms, straight-chain or branched alkoxy having up to 4 carbon atoms, or benzyloxy, and R$^2$ and R$^3$ represent hydrogen or represent NHR$^5$, R$^5$ having the same meaning as R$^1$ and being identical to or different from the latter, with the proviso that, in every case, one substituent of R$^2$ or R$^3$ represents hydrogen and the other substituent of R$^2$ or R$^3$ represents NHR$^5$, and physiologically acceptable salts thereof.

3. A 3-amino-4,5-dihydroxypiperidine according to claim 1, in which

R$^1$ represents hydrogen, alkyl having up to 4 carbon atoms, benzyl, acetyl or benzyloxycarbonyl, and R$^2$ and R$^3$ represent hydrogen or represent the group NHR$^5$, R$^5$ having the same meaning as R$^1$ and being identical to or different from the latter, with the proviso that, in every case, one substituent of R$^2$ or R$^3$ represents hydrogen and the other substituent of R$^2$ R$^3$ represents NHR$^5$, and physiologically acceptable salts thereof.

4. A 3-amino-4,5-dihydroxypiperidine according to claim 1, having the manno configuration (Ia)

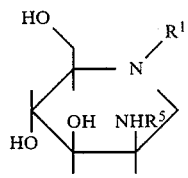 (Ia)

5. A 3-amino-4,5-dihydroxypiperidine according to claim 1, having the gluco configuration (Ib)

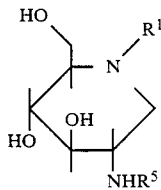 (Ib)

6. A 3-amino-4,5-dihydroxypiperidine according to claim 1 selected from the group consisting of
2-acetamido-1,5-imino-1,2,5-trideoxy-D-mannitol,
2amino-1,5-imino-1,2,5-trideoxy-D-mannitol,
2-acetamido-1,2-dideoxy-nojirimycin,
2-acetamido-N-benzyl-1,2-dideoxy-nojirimycin, and
2-acetamido-N-methyl-1,2-dideoxy-nojirimycin.

7. A method of treating prediabetes in a patient which comprises administering to said patient a therapeutically effective amount of a 3-amino-4,5-dihydroxypiperidine according to claim 1 sufficient to treat prediabetes in said patient.

8. A method according to claim 7, wherein the 3-amino-4,5-dihydroxypiperidine is selected from the group consisting of
2-acetamido-1,5-imino-1,2,5-trideoxy-D-mannitol,
2-amino-1,5-imino-1,2,5-trideoxy-D-mannitol,
2-acetamido-1,2-dideoxy-nojirimycin,
2-acetamido-N-benzyl-1,2-dideoxy-nojirimycin, and
2-acetamido-N-methyl-1,2-dideoxy-nojirimycin.

9. A medicament composition comprising a pharmaceutically effective amount of a 3-amino-4,5-dihydroxypiperidine according to claim 1 in admixture with a pharmaceutically acceptable carrier.

10. A unit dose of a composition according to claim 8 in the form of a tablet, capsule, suspension, solution, syrup or elixir.

11. A method of treating gastritis in a patient which comprises administering to said patient a therapeutically effective amount of a 3-amino-4,5-dihydroxypiperidine according to claim 1 sufficient to treat gastritis in said patient.

12. A method of treating constipation in a patient which comprisesadministering to said patient a therapeutically effective amount of a 3-amino-4,5-dihydroxypiperidine according to claim 1 sufficient to treat constipation in said patient.

13. A method of treating caries in a patient which comprises administering to said patient a therapeutically effective amount of a 3-amino-4,5-dihydroxypiperidine according to claim 1 sufficient to treat caries in said patient.

14. A method of treating artherosclerosis in a patient which comprises administering to said patient a therapeutically effective amount of a 3-amino-4,5-dihydroxypiperidine according to claim 1 sufficient to treat artherosclerosis in said patient.

15. A method of treating obesity in a patient which comprises administering to said patient a therapeutically effective amount of a 3-amino-4,5-dihydroxypiperidine according to claim 1 sufficient to treat obesity in said patient.

16. A method of treating diabetes in a patient which comprises administering to said patient a therapeutically effective amount of a 3-amino-4,5-dihydroxypiperidine according to claim 1 sufficient to treat diabetes in said patient.

17. A method of treating hyperlipoproteinaemia in a patient which comprises administering to said patient a therapeutically effective amount of a 3-amino-4,5-dihydroxypiperidine according to claim 1 sufficient to treat hyperlipoproteinaemia in said patient.

18. A 3-amino-4,5-dihydroxypiperidine according to claim 1, wherein the salt is selected form the group consisting of hydrochlorides, hydrobromides, sulphates, hydrogen sulphates, hydrogen phosphates, hydrogen carbonates, carbonates, phosphates, acetates, maleates, citrates, fumarates, oxalates and benzoates.

19. A method of increasing the ratio of desired low-fat meat/undesired fat in an animal comprising administering to said animal a fat reducing effective amount of a 3-amino-4,5-dihdyroxypiperidine according to claim 1.

* * * * *